(12) United States Patent
Farese

(10) Patent No.: US 8,580,769 B2
(45) Date of Patent: Nov. 12, 2013

(54) TREATMENT OF OBESITY, METABOLIC SYNDROME, AND DIABETES WITH PROTEIN KINASE C INHIBITORS

(75) Inventor: Robert V. Farese, St. Petersburg, FL (US)

(73) Assignees: The United States of America as represented by the Department of Veterans Affairs, Washington, DC (US); The Roskamp Institute, Sarasota, FL (US)

( * ) Notice: Subject to any disclaimer, the term of this patent is extended or adjusted under 35 U.S.C. 154(b) by 0 days.

(21) Appl. No.: 13/417,075

(22) Filed: Mar. 9, 2012

(65) Prior Publication Data

US 2012/0232037 A1  Sep. 13, 2012

Related U.S. Application Data

(60) Provisional application No. 61/451,417, filed on Mar. 10, 2011.

(51) Int. Cl.
| | |
|---|---|
| A61K 31/675 | (2006.01) |
| A61K 31/28 | (2006.01) |
| A61K 31/4164 | (2006.01) |
| A61K 31/155 | (2006.01) |

(52) U.S. Cl.
USPC .............. 514/94; 514/400; 514/495; 514/635

(58) Field of Classification Search
USPC ................... 514/94, 400, 495, 635
See application file for complete search history.

(56) References Cited

U.S. PATENT DOCUMENTS

| | | | |
|---|---|---|---|
| 1,994,213 | A | 3/1935 | Delépine |
| 4,165,380 | A | 8/1979 | Hill |
| 4,599,436 | A | 7/1986 | Harvey et al. |
| 2003/0212014 | A1 | 11/2003 | Ruderman et al. |
| 2009/0075932 | A1 | 3/2009 | Acevedo-Duncan et al. |
| 2009/0130195 | A1 | 5/2009 | Acevedo-Duncan et al. |
| 2010/0092578 | A1 | 4/2010 | Fields et al. |

OTHER PUBLICATIONS

Erdogan et al., "Aurothiomalate Inhibits Transformed Growth by Targeting the PB1 Domain of Protein Kinase Cι," *Journal of Biological Chemistry*, vol. 281, pp. 28450-28459, 2006.

Farese and Sajan, "Metabolic functions of atypical protein kinase C: 'good' and 'bad' as defined by nutritional status," *Am. J. Physiol. Endocrinol. Metab.*, vol. 298, pp. E385-E394, 2010.

Farese et al., "Muscle-specific knockout of PKC-λ impairs glucose transport and induces metabolic and diabetic syndromes," *J. Clin. Invest.*, vol. 117, pp. 2289-2301, 2007.

Fields and Regala, "Protein kinase Cι: human oncogene, prognostic marker and therapeutic target," *Pharmacol Res.*, vol. 55, pp. 487-497, 2007 (19 pages; Public Access Author Manuscript version).

Hashimoto et al., "Immunomodulatory Effects of Therapeutic Gold Compounds: Gold Sodium Thiomalate Inhibits the Activity of T Cell Protein Kinase C," *J. Clin. Invest.*, vol. 89, pp. 1839-1848, 1992.

Kean and Hogan, "Gold Therapy: I. Historical, Chemical, Pharmacological and Biological Profile of Anti-Arthritic Gold Compounds," *Singapore Medical Journal*, vol. 28, pp. 110-116, 1987.

Matsumoto et al., "PKCλ in liver mediates insulin-induced SREBP-1c expression and determines both hepatic lipid content and overall insulin sensitivity," *J. Clin. Invest.*, vol. 112, pp. 935-944, 2003.

Mayer and Marshall, "Specificity of Gold Thioglucose for Ventromedial Hypothalamic Lesions and Hyperphagia," *Nature*, vol. 178, pp. 1399-1400, 1956 (Abstract only).

Regala et al., "Atypical Protein Kinase Cι Expression and Aurothiomalate Sensitivity in Human lung Cancer Cells," *Cancer Research*, vol. 68, pp. 5888-5895, 2008.

Sajan et al., "The critical role of atypical protein kinase C in activating hepatic SREBP-1c and NFκB in obesity," *J. Lipid Res.*, vol. 50, pp. 1133-1145, 2009.

Sajan et al., "Correction of metabolic abnormalities in a rodent model of obesity, metabolic syndrome, and type 2 diabetes mellitus by inhibitors of hepatic protein kinase C-ι," *Metabolism*, doi:10.1016/j.metabol.2011.12.008, 2012 (11 pages).

Sajan and Farese, "Insulin signalling in hepatocytes of humans with type 2 diabetes: excessive production and activity of protein kinase C-ι (PKC-ι) and dependent processes and reversal by PKC-ι inhibitors," *Diabetologia*, doi:10.1007/s00125-012-2477-5, 2012 (12 pages).

Stallings-Mann et al., "A Novel Small-Molecule Inhibitor of Protein Kinase Cι Blocks Transformed Growth of Non-Small-Cell Lung Cancer Cells," *Cancer Research*, vol. 66, pp. 1767-1774, 2006.

*Primary Examiner* — Raymond Henley, III
(74) *Attorney, Agent, or Firm* — Klarquist Sparkman, LLP

(57) ABSTRACT

Disclosed herein are methods for treating obesity, metabolic syndrome, diabetes, or a combination of these conditions. The methods include selecting a subject with obesity, metabolic syndrome, or diabetes and administering to the subject a therapeutically effective amount of a composition comprising a compound that specifically inhibits hepatic protein kinase C (PKC)-ι, thereby treating the obesity, metabolic syndrome, or diabetes in the subject. In some embodiments the compound that specifically inhibits hepatic PKC-ι includes a thio-gold compound (such as aurothiomalate, aurothioglucose, and auranofin) or a derivative thereof, or a pharmaceutically acceptable salt thereof. In other embodiments, the compound that specifically inhibits hepatic PKC-ι includes 1H-imidazole-4-carboxamide, 5-amino-1-[2,3-dihydroxy-4-[(phosphonooxy)methyl]cyclopentyl]-[1R-(1α, 2β,3β,4α)] (ICAPP) or a derivative thereof, or a pharmaceutically acceptable salt thereof.

20 Claims, 19 Drawing Sheets

FIG. 8A
FIG. 8B
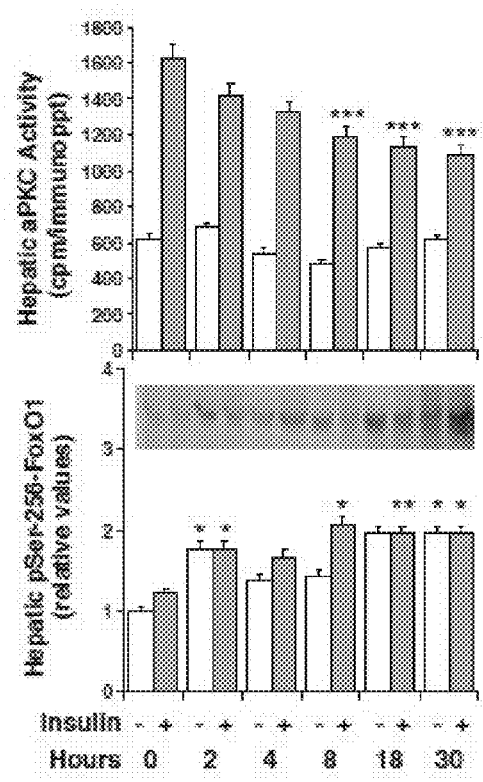
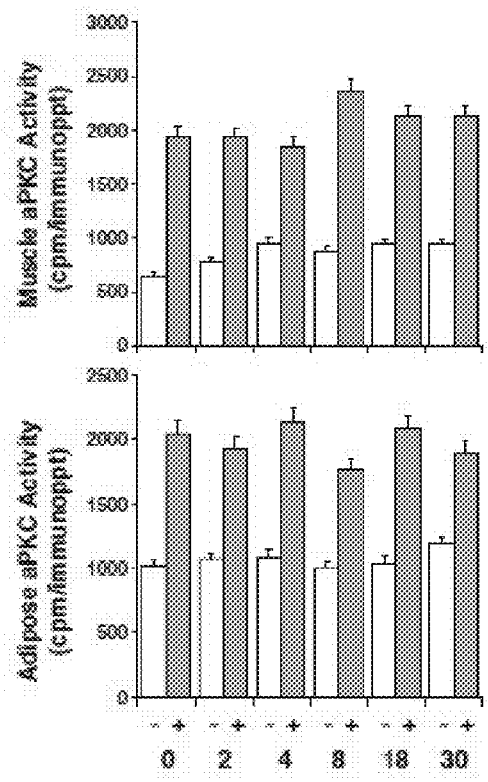
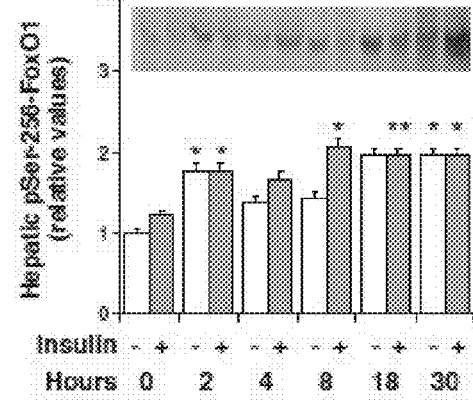
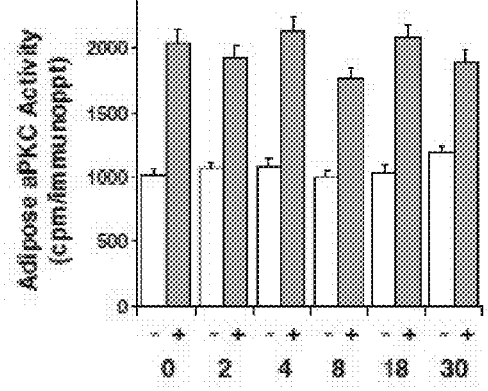
FIG. 8C
FIG. 8D

TREATMENT OF OBESITY, METABOLIC SYNDROME, AND DIABETES WITH PROTEIN KINASE C INHIBITORS

CROSS REFERENCE TO RELATED APPLICATION

This claims the benefit of U.S. Provisional Application No. 61/451,417, filed Mar. 10, 2011, which is incorporated herein by reference in its entirety.

ACKNOWLEDGMENT OF GOVERNMENT SUPPORT

This invention was made with government support under grant number RO1DK065969 awarded by the National Institutes of Health and a VA Merit Review Grant awarded by the Department of Veterans Affairs. The government has certain rights in the invention.

FIELD

This disclosure relates to methods for treating obesity, metabolic syndrome, and diabetes, particularly using protein kinase C inhibitors.

BACKGROUND

The interrelated disorders of obesity (O), metabolic syndrome (MS), type 2 diabetes mellitus (T2DM), and associated cardiovascular disorders rank amongst the most important health problems facing Western and Westernized populations. Clinical abnormalities in these disorders, including obesity, hyper/dyslipidemia, insulin resistance, and glucose intolerance are each independent cardiovascular risk factors that are usually treated piecemeal and with limited success. In insulin-resistant states of O/MS/T2DM, insulin effects on hepatic lipid synthesis are conserved, even when effects on hepatic glucose production are diminished, as in overt T2DM. This paradox in T2DM results in hyper/dyslipidemia and hyperglycemia, a lethal combination for developing cardiovascular disease.

New approaches are needed to contain the costly pandemic of O/MS/T2DM. Identifying a unifying pathogenetic factor for these risk factors that could serve as a single therapeutic target would simplify this task.

SUMMARY

Disclosed herein are methods for treating obesity, metabolic syndrome, diabetes, or a combination of these conditions. The methods include selecting a subject with obesity, metabolic syndrome, and/or diabetes (for example, T2DM) and administering to the subject a therapeutically effective amount of a composition comprising a compound that specifically inhibits protein kinase C (PKC)$_{-\iota}$, thereby treating the obesity, metabolic syndrome, or diabetes in the subject. In some examples, the compound specifically inhibits hepatic PKC$_{-\iota}$. In specific examples, the compound does not substantially inhibit PKC$_{-\iota}$ in muscle or adipose tissue. In further examples, the compound is not a protein or a nucleic acid.

In some embodiments the compound that specifically inhibits hepatic PKC$_{-\iota}$ includes a thio-gold compound. Thio-gold compounds of use in the disclosed methods include but are not limited to aurothiomalate (ATM), aurothioglucose (ATG), and auranofin. In some examples, the thio-gold compound is a pharmaceutically acceptable salt, for example, a sodium or disodium salt.

In other embodiments, the compound that specifically inhibits hepatic PKC$_{-\iota}$ includes 1H-imidazole-4-carboxamide, 5-amino-1-[2,3-dihydroxy-4-[(phosphonooxy)methyl]cyclopentyl]-[1R-(1α,2β,3β,4α)] (ICAPP) or a derivative thereof. In some examples, ICAPP or the derivative thereof is a pharmaceutically acceptable salt.

The disclosed methods treat (for example, inhibit or even prevent) obesity, metabolic syndrome, and/or diabetes, for example by increasing glucose tolerance, decreasing insulin resistance, decreasing serum triglycerides, decreasing serum free fatty acid levels, decreasing total serum cholesterol, decreasing serum low-density lipoprotein, increasing serum high-density lipoprotein, decreasing HbA1c levels, decreasing body weight, decreasing hepatosteatosis, or a combination of two or more thereof in the subject, for example as compared to a control.

In some embodiments, the disclosed methods further include providing a second therapy to the subject, such as a lifestyle modification, antihyperglycemic agents, insulin, glucagon-like peptide (GLP), dipeptidyl peptidase-4 inhibitors, thiazolidinediones, lipid lowering compounds, or a combination of two or more thereof.

The foregoing and other features of the disclosure will become more apparent from the following detailed description, which proceeds with reference to the accompanying figures.

BRIEF DESCRIPTION OF THE DRAWINGS

FIG. 2A is a graph showing basal and insulin-stimulated aPKC activity. FIG. 2B is a graph showing basal and insulin-stimulated Akt activity. FIG. 2C is a digital image of a representative immunoblot of levels of IRS-1 and IRS-2, phosphorylation of the auto(trans)phosphorylation site of PKC$_{-\iota}$/ζ (threonine-555/560) and PDK2-dependent site of Akt½ (serine-473), and levels of PKC$_{-\iota}$, PKC$_{-\iota}$/ζ (total aPKC), and Akt½. Hepatocytes of all subjects (5 non-diabetic and 5 type 2 diabetic (T2DM)) were compared simultaneously during a 15-minute incubation. Bar graph values are mean±SEM of 5 patients. P values (ANOVA) are shown for bracketed comparisons.

FIG. 3A is a bar graph showing basal and insulin-stimulated aPKC activity. FIG. 3B is a bar graph showing Akt2 activity. FIGS. 3C and 3D are bar graphs showing PKC$_{-\iota}$ and PKCζ mRNA levels, respectively. FIG. 3E is a digital image of a representative immunoblot of phospho-threonine-555/560-PKC$_{-\iota}$/ζ, PKC$_{-\iota}$, PKC-ζ and PKC$_{-\iota}$/ζ (total aPKC). FIGS. 3F-L are a series of bar graphs showing expression of lipogenic (SREBP-1c, FAS, and ACC), glucogenic (PEPCK, G6 Pase), and inflammatory (TNF-α and IL-1β) markers. Incubation time, 4 or 6 hours (values were comparable at both times and therefore pooled). Bar graph values (all normalized to unity) are mean±SEM of the number of patients shown in parentheses. Brackets and asterisks reflect significant differences (*, P<0.05; , P<0.01: *, P<0.001; ANOVA) between indicated groups.

FIG. 4A is a bar graph showing the effect of ICAPP on phosphatidylinositol-3,4,5-$(PO_4)_3$ ($PIP_3$)-stimulated $PKC_{-\iota}$ activity (10 ng recombinant $PKC_{-\iota}$ activated by 10 fM $PIP_3$). FIGS. 4B and 4E are bar graphs showing the effect of ICAPP on basal and insulin-stimulated activities of total aPKC and Akt2. FIGS. 4C, D, and F-J are bar graphs showing expression of lipogenic (SREBP-1c, FAS, and ACC), inflammatory (TNF-αc and IL-1β), and glucogenic (PEPCK and G6 Pase) markers in basal and insulin-stimulated cells treated with ICAPP. FIG. 4K is a bar graph and digital image showing serine-256 phosphorylation of FoxO1 in hepatocytes. Incubation time, 4 hours. Values are mean±SEM of 4 or more determinations in a single experiment.

FIGS. 5A and 5D are bar graphs showing the effect of ATM on basal and insulin-stimulated activities of total aPKC and Akt2. FIGS. 5B, C and E-I are bar graphs showing expression of lipogenic (SREBP-1c, FAS, and ACC), inflammatory (TNF-αc and IL-1β), and glucogenic (PEPCK and G6 Pase) enzymes in basal and insulin-stimulated cells treated with ATM. Incubation time, 4 hours. Values are mean±SEM of 4 or more determinations in a single experiment.

FIGS. 6A-F is a series of bar graphs showing the effect of ATM on basal and insulin-stimulated activities of total aPKC and Akt2 in liver, muscle and adipose tissues. FIGS. 6M-R is a series of bar graphs showing expression of lipogenic (SREBP-1c, FAS, and ACC) and glucogenic (PEPCK, G6 Pase) markers and nuclear levels of the active NFκB/p65/RelA subunit in liver of mice treated with ATM. Het-MλKO mice were treated with vehicle (Veh) or ATM in vehicle (60 mg/kg body weight/day) for 7 days, and on the $8^{th}$ day the Het-MλKO mice, along with littermate wild type (WT) mice, were treated for 15 minutes by intraperitoneal injection with vehicle alone (−) or with vehicle containing insulin (1 U/kg body weight) (+). Values are mean±SEM of the number of mice shown in parentheses. RU=relative units. P values (ANOVA) reflect comparisons between indicated groups.

FIGS. 7A-F is a series of bar graphs showing the effect of ICAPP on basal and insulin-stimulated activities of total aPKC and Akt2 in liver, muscle and adipose tissues. FIGS. 7 G-L and R is a series of bar graphs showing clinical parameters (abdominal fat, serum cholesterol, serum and liver triglycerides, serum glucose, serum insulin, and serum free fatty acids) in mice treated with ICAPP.

FIGS. 8A-D is a series of bar graphs showing inhibition of hepatic aPKC during ICAPP treatment in vivo. Wild type mice were treated with 1.5 mg/kg ICAPP subcutaneously and treated with or without 1 U/kg insulin at the indicated times. FIG. 8A shows hepatic aPKC activity. FIG. 8B shows muscle aPKC activity. FIG. 8C shows p-Ser-256-FoxO1 in liver (inset: digital image of a representative Western blot). FIG. 8D shows adipose tissue aPKC activity. Values are mean±SEM of 6 to 8 determinations. *p<0.05; p<0.01; *p<0.001 (ANOVA).

SEQUENCE LISTING

Any nucleic acid and amino acid sequences listed herein or in the accompanying Sequence Listing are shown using standard letter abbreviations for nucleotide bases, and three letter code for amino acids, as defined in 37 C.F.R. §1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Mar. 1, 2012, and is 8606 bytes, which is incorporated by reference herein.

SEQ ID NOS: 1-40 are nucleic acid sequences of primers utilized for reverse transcription polymerase chain reactions.

Figure 1:
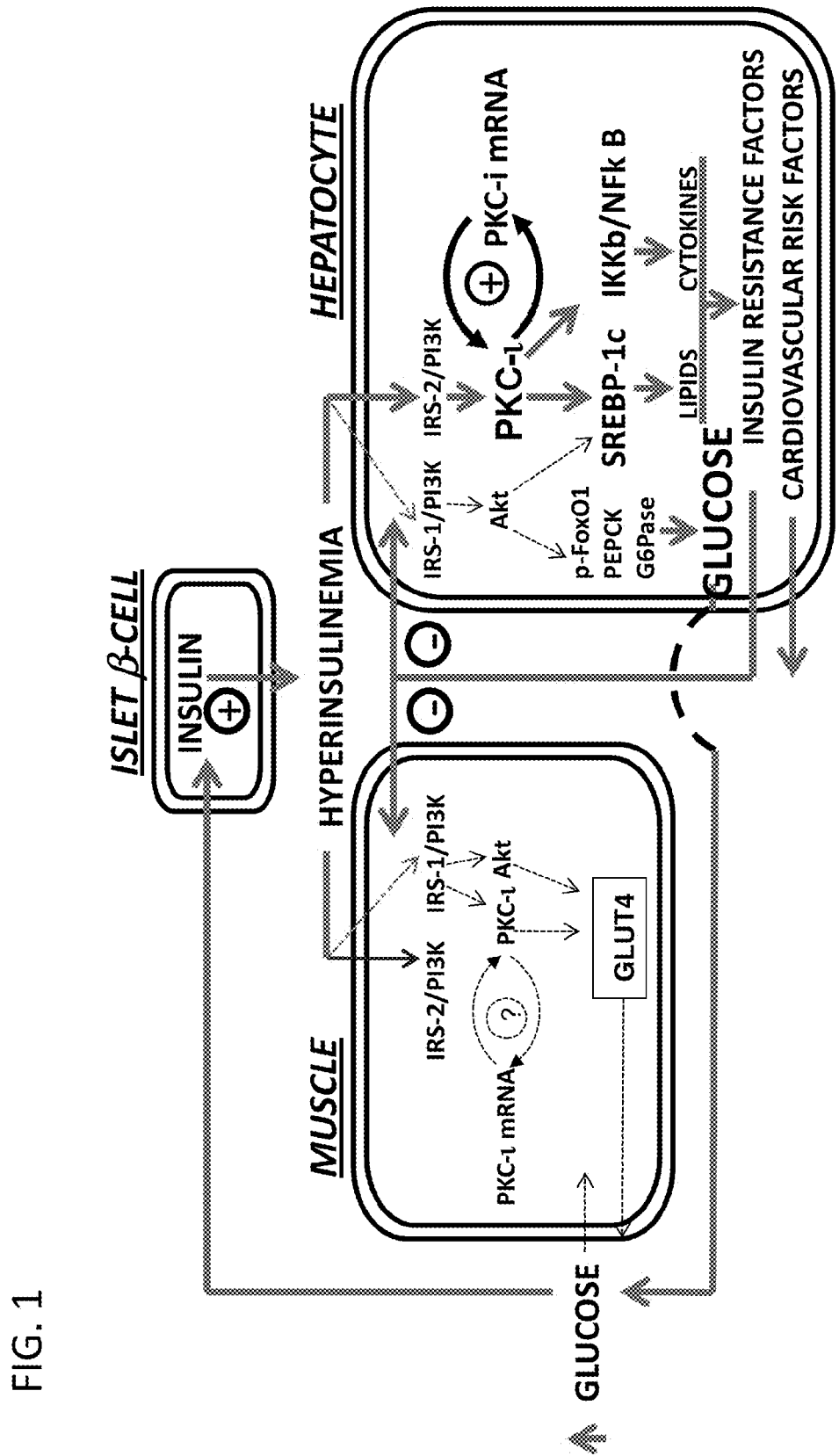
FIG. 1 is a schematic of effects of PKC$_{-\iota}$ activity in muscle and liver of a subject with obesity, metabolic syndrome, or diabetes. Over-expression and/or over-activation of PKC$_{-\iota}$ in hepatocytes (for example, as a result of hyperinsulinemia) promote lipogenic, inflammatory, and gluconeogenic pathways, leading to insulin resistance and other clinical abnormalities. In contrast PKC$_{-\iota}$ is under-expressed and/or under-activated in skeletal muscle, leading to hyperglycemia.

DETAILED DESCRIPTION $PKC_{-\iota}$ expression and/or activity is increased in hepatocytes of subjects with T2DM, but is decreased in muscle. The decreased expression/activation of $PKC_{-\iota}$ and glucose transport in muscle causes or exacerbates glucose intolerance and hyperinsulinemia, which in turn increases hepatic $PKC_{-\iota}$ expression/activation and expression of lipogenic, inflammatory, and gluconeogenic pathways, thereby provoking further increases in glucose intolerance and diminishing insulin signaling to IRS -1/PI3K, $PKC_{-\iota}$, and Akt in liver, and IRS-2/PI3K and Akt in muscle (FIG. 1). Without being bound by theory, this imbalance between muscles and liver $PKC_{-\iota}$ in diabetes appears to be a multi-organ vicious cycle that is superimposed on the vicious cycle of $PKC_{-\iota}$ over-activation of lipogenic, inflammatory, glucogenic pathways in the liver.

Disclosed herein are methods of treating obesity, metabolic syndrome, and/or obesity in a subject including administering to a subject a therapeutically effective amount of a composition including a compound that specifically inhibits hepatic $PKC_{-\iota}$. The inventor found that a thio-gold compound (such as ATM) or the compound ICAPP inhibited basal and insulin-stimulated $PKC_{-\iota}$, but not Akt activity and also inhibited expression of lipogenic, inflammatory, and glucogenic genes in hepatocytes isolated from non-diabetic and T2DM subjects. Surprisingly, these compounds selectively inhibited $PKC_{-\iota}$ in hepatic tissue, but not in muscle or adipose tissue, and improved clinical parameters of insulin resistance, glucose intolerance, hepatosteatosis, abdominal obesity, hypertriglyceridemia, and hypercholesterolemia. This interrupts the insulin-driven cycle of over-expressed and/or over-active $PKC_{-\iota}$ that contributes to the clinical abnormalities associated with obesity, metabolic syndrome, and diabetes.

I. Abbreviations
ACC acetyl CoA carboxylase
aPKC atypical protein kinase C
ATM aurothiomalate
BMI body mass index
FAS fatty acid synthase
FPG fasting plasma glucose
G6 Pase glucose-6-phosphatase
HbA1c hemoglobin A1c
HDL high-density lipoprotein
ICAP 1H-imidazole-4-carboxamide 5-amino-1-[2,3-dihydroxy-4-[hydroxymethyl]cyclopentyl]-[1R-(1α,2β,3β,4α)] (non-phosphorylated form of ICAPP)
ICAPP 1H-imidazole-4-carboxamide, 5-amino-1-[2,3-dihydroxy-4-[(phosphonooxy)methyl]cyclopentyl]-[1R-(1α, 2β,3β,4α)]
IGT impaired glucose tolerance
IL-1β interleukin-1β
LDL low-density lipoprotein
MS metabolic syndrome
O obesity
OGTT oral glucose tolerance test
PEPCK phosphoenolpyruvate carboxykinase
$PIP_3$ phosphatidylinositol-3,4,5-$(PO_4)_3$
PKC protein kinase C
$PKC_{-t}$ PKC-iota
QUICKI quantitative insulin sensitivity check index
SREBP-1c sterol receptor element binding protein-1c
T2DM type 2 diabetes
TNF-α tumor necrosis factor-α

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. As used herein, "comprises" means "includes." Thus, "comprising A or B," means "including A, B, or A and B," without excluding additional elements. It is further to be understood that all base sizes or amino acid sizes, and all molecular weight or molecular mass values, given for nucleic acids or polypeptides are approximate, and are provided for description. All publications, patent applications, patents, and other references mentioned herein are incorporated by reference in their entirety for all purposes.

Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

In order to facilitate review of the various embodiments of the invention, the following explanations of specific terms are provided:

Aurothiomalate (ATM): Also known as (auriosulfanyl)-3-carboxypropanoate. ATM is an example of a thio-gold compound. In some examples, ATM includes a pharmaceutically acceptable salt of ATM (such as a sodium salt, for example sodium ATM or disodium ATM), such as $C_4H_4AuNaa_4S$ or $C_4H_3AuNa_2O_4S$. In some non-limiting examples, ATM has one of the following structures:

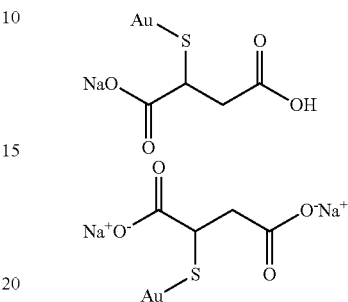

In one example, ATM includes MYOCRISIN® (Sanofi-Aventis) or MYOCHRYSINE® (Akorn, Inc.).

Body mass index (BMI): A mathematical formula for measuring body mass in humans, also sometimes called Quetelet's Index. BMI is calculated by dividing weight (in kg) by $height^2$ (in $meters^2$). The current standard for both men and women accepted as "normal" is a BMI of 20-24.9 $kg/m^2$. In one embodiment, a BMI of greater than 25 $kg/m^2$ can be used to identify an obese subject. Grade I obesity (also called "overweight") corresponds to a BMI of 25-29.9 $kg/m^2$. Grade II obesity corresponds to a BMI of 30-40 $kg/m^2$; and Grade III obesity corresponds to a BMI greater than 40 $kg/m^2$ (Jequier, *Am. J. Clin. Nutr.*, 45:1035-47, 1987). Ideal body weight will vary among individuals based on height, body build, bone structure, and sex.

Derivative: A compound or portion of a compound that is derived from or is theoretically derivable from a parent compound, for example if at least one atom is replaced with another atom or group of atoms. Derivatives also include compounds to which at least one atom or functional group is added or removed, rather than replacing an atom or functional group of the parent compound.

Diabetes Mellitus: A disease caused by a relative or absolute lack of insulin leading to uncontrolled carbohydrate metabolism, commonly simplified to "diabetes," though diabetes mellitus should not be confused with diabetes insipidus. As used herein, "diabetes" refers to diabetes mellitus, unless otherwise indicated. A "diabetic condition" includes pre-diabetes and diabetes. Type 1 diabetes (sometimes referred to as "insulin-dependent diabetes" or "juvenile-onset diabetes") is an auto-immune disease characterized by destruction of the pancreatic β cells that leads to a total or near total lack of insulin. In type 2 diabetes (T2DM; sometimes referred to as "non-insulin-dependent diabetes" or "adult-onset diabetes"), the body does not respond to insulin, though it is present.

Symptoms of diabetes include: excessive thirst (polydipsia); frequent urination (polyuria); extreme hunger or constant eating (polyphagia); unexplained weight loss; presence of glucose in the urine (glycosuria); tiredness or fatigue; changes in vision; numbness or tingling in the extremities (hands, feet); slow-healing wounds or sores; and abnormally high frequency of infection. Diabetes may be clinically diagnosed by a fasting plasma glucose (FPG) concentration of greater than or equal to 7.0 mmol/L (126 mg/dL), or a plasma glucose concentration of greater than or equal to 11.1 mmol/L (200 mg/dL) at about two hours after an oral glucose tolerance test (OGTT) with a 75 g load. A more detailed description of diabetes may be found in *Cecil Textbook of Medicine*, J. B. Wyngaarden, et al., eds. (W.B. Saunders Co., Philadelphia, 1992, 19th ed.).

1H-imidazole-4-carboxamide, 5-amino-1-[2,3-dihydroxy-4-[(phosphonooxy)methyl]cyclopentyl]-[1R-(1α,2β, 3β,4α)] (ICAPP): A compound having the following structure:

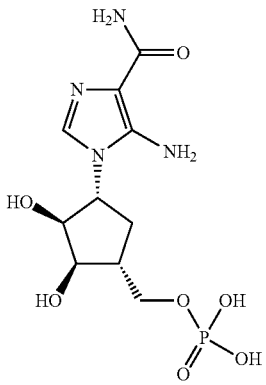 [SMILES: NC(=O)c1ncn([C@@H]2C[C@H](COP(=O)(O)O)[C@@H](O)[C@H]2O)c1N]

(also known as [(1R,2R,3S,4R)-4-(5-amino-4-carbamoylimidazol-1-yl)-2,3-dihydroxycyclopentyl]methyl dihydrogen phosphate). The disclosed compounds also include derivatives of ICAPP, in which at least one atom or functional group is added, removed, or replaced by at least one other atom or functional group. In particular examples, derivatives of ICAPP retain the phosphate and cyclopentyl groups. In another example, a derivative of ICAPP includes the dephosphorylated form (ICAP), which can be phosphorylated in liver and other mammalian tissues to form ICAPP.

Insulin Resistance: A state in which the cells of a subject do not respond appropriately to insulin, and increased amounts of insulin are required for glucose to be taken up by the cells. In some examples, insulin resistance is defined as a state where 200 units of insulin per day or more are required to attain glycemic control and prevent ketosis. Subjects with insulin resistance often have increased plasma glucose levels, increased plasma insulin levels, or both, as compared with a subject without insulin resistance or standard normal ranges.

In some examples, insulin resistance is determined by measuring blood glucose (such as fasting plasma glucose) and/or blood insulin (such as fasting plasma insulin) levels. In other examples, insulin resistance is determined by oral glucose tolerance test, glucose clamp (such as hyperinsulinemic euglycemic clamp), modified insulin suppression test, homeostatic model assessment, or quantitative insulin sensitivity check index (QUICKI).

Metabolic Syndrome: A group of metabolic risk factors, including abdominal obesity, atherogenic dyslipidemia, elevated blood pressure, insulin resistance, pro-thrombotic state, and pro-inflammatory state, that correlate with increased risk of coronary heart disease, stroke, and type 2 diabetes. As much as 20-25% of the adult population worldwide is estimated to have metabolic syndrome. Treatment of metabolic syndrome currently includes lifestyle changes (including weight loss and increased physical activity). If lifestyle changes are not effective, drug therapy for individual components of the metabolic syndrome (such as cholesterol lowering drugs and anti-hypertensives) can be administered.

There are a number of different guidelines for diagnosing metabolic syndrome. In one example, metabolic syndrome is diagnosed using the National Cholesterol Education Program Adult Treatment Panel III (NCEP ATPIII) criteria, which include at least three of: central obesity (waist circumference ≥40 inches (male) or ≥36 inches (female)), triglycerides ≥1.7 mM (150 mg/dL), high density lipoprotein (HDL) <40 mg/dL (male) or <50 mg/dL (female), blood pressure ≥130/85 mm Hg, and fasting plasma glucose ≥6.1 mM (110 mg/dL). In another example, metabolic syndrome is diagnosed using the International Diabetes Federation criteria, which include central obesity (waist circumference based on ethnic specific values or body mass index >30 kg/m$^2$) and any two of: triglycerides of ≥150 mg/dL or specific treatment for this lipid abnormality, HDL <40 mg/dL (male) or <50 mg/dL (female) or specific treatment for this lipid abnormality, systolic blood pressure ≥135 mm Hg or diastolic blood pressure ≥85 mm Hg or treatment of previously diagnosed hypertension, and fasting plasma glucose ≥100 mg/dL or previously diagnosed type 2 diabetes. See, e.g., Expert Panel on Detection, Evaluation, and Treatment of High Blood Cholesterol in Adults, *J. Am. Med. Assn.* 285:2486-2497, 2001; Alberti et al., *Diabet. Med.* 23:469-480, 2006.

Obesity: A condition in which excess body fat may put a person at health risk (see Barlow and Dietz, *Pediatrics* 102: E29, 1998; National Institutes of Health, *Obes. Res.* 6 (suppl. 2):515-2095, 1998). Excess body fat is a result of an imbalance of energy intake and energy expenditure. In one embodiment in humans, the Body Mass Index (BMI) is used to assess obesity. In one embodiment, a BMI of 25.0 kg/m$^2$ to 29.9 kg/m$^2$ is overweight (also called grade I obesity), while a BMI of 30 kg/m$^2$ is truly obese (also called grade II obesity).

In another embodiment in humans, waist circumference is used to assess obesity. In this embodiment, in men a waist circumference of 102 cm or more is considered obese, while in women a waist circumference of 89 cm or more is considered obese. Strong evidence shows that obesity affects both the morbidity and mortality of individuals. For example, an obese individual is at increased risk for heart disease, non-insulin dependent (type 2) diabetes, hypertension, stroke, cancer (e.g. endometrial, breast, prostate, and colon cancer), dyslipidemia, gall bladder disease, sleep apnea, reduced fertility, and osteoarthritis, amongst others (see Lyznicki et al., Am. Fam. Phys. 63:2185, 2001).

Pharmaceutically Acceptable Carrier: The pharmaceutically acceptable carriers useful in this disclosure are conventional. *Remington: The Science and Practice of Pharmacy*, The University of the Sciences in Philadelphia, Editor, Lippincott, Williams, & Wilkins, Philadelphia, Pa., 21st Edition (2005), describes compositions and formulations suitable for pharmaceutical delivery of compounds, such as an inhibitor of PKC$_{-ι}$ (for example, ATM or ICAPP).

In general, the nature of the carrier will depend on the particular mode of administration employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate.

Protein Kinase C (PKC): A family of serine/threonine protein kinases including at least ten isozymes. PKC members are divided into three subfamilies based on the second messenger signaling which activates them. The three subfamilies are the conventional PKCs (cPKCs), the novel PKCs (nPKCs), and the atypical PKCs (aPKCs). The cPKCs require diacylglycerol (DAG), calcium, and phospholipids (such as phosphatidylserine) for activation and include PKC-α, PKC- β, and PKC-γ. The nPKCs require DAG but no calcium for activation and include PKC-δ, PKC-ε, PKC-η, and PKC-θ. The aPKCs include PCK-ι and PKC-ζ and do not require either calcium or DAG for activation.

$PKC_{-\iota}$ is an atypical PKC; it is calcium-independent and is not activated by DAG or phorbol esters, but is phospholipid-dependent. $PKC_{-\iota}$ is ubiquitously expressed in mammals. The mouse ortholog of $PKC_{-\iota}$ is referred to as PKC-λ.

Nucleic acid and protein sequences for $PKC_{-\iota}$ (gene symbol: PKCI) are publicly available. For example, GenBank Accession No. NM_002740 discloses an exemplary human $PKC_{-\iota}$ nucleic acid sequence, and GenBank Accession No. NP_002731 discloses an exemplary human $PKC_{-\iota}$ amino acid sequence, both of which are incorporated by reference as provided by GenBank on Mar. 10, 2011. Similarly, GenBank Accession No. NM_008857 discloses an exemplary mouse $PKC_{-\iota}$ (PKC-λ) nucleic acid sequence, and GenBank Accession No. NP_032883 discloses an exemplary mouse $PKC_{-\iota}$ (PKC-λ) amino acid sequence, both of which are incorporated by reference as provided by GenBank on Mar. 10, 2011.

In one example, $PKC_{-\iota}$ includes a full-length wild-type (or native) sequence, as well as $PKC_{-\iota}$ allelic variants that retain protein kinase activity. In certain examples, $PKC_{-\iota}$ has at least 80% sequence identity, for example at least 85%, 90%, 95%, or 98% sequence identity to a publicly available $PKC_{-\iota}$ sequence, such as those referenced above.

Purified: The term purified does not require absolute purity; rather, it is intended as a relative term. Thus, for example, a purified preparation of a PKC inhibitor (such as an inhibitor of $PKC_{-\iota}$) is one in which the PKC inhibitor is more enriched than in its environment within a cell or other preparation, such as the environment in which it is synthesized. Preferably, a preparation is purified such that the PKC inhibitor represents at least 50% of the total content of the preparation, for example, at least 50% by weight. In one embodiment, the PKC inhibitor is at least 50%, for example at least 70%, at least 75%, at least 80%, at least 85%, at least 90%, at least 95%, or more free of proteins, lipids, carbohydrates or other materials with which it is originally associated.

Specific Inhibitor: An agent that substantially or preferentially inhibits (for example, decreases expression or activity of) only a defined target such as a protein or enzyme. In an example, a compound that "specifically inhibits" a target decreases expression or activity of an atypical PKC, such as $PKC_{-\iota}$. In some examples, the specific inhibitor decreases expression or activity of the PKC in a particular tissue (such as liver). In one example, a disclosed compound specifically inhibits $PKC_{-\iota}$ in the liver (hepatic $PKC_{-\iota}$), but does not substantially inhibit $PKC_{-\iota}$ in muscle or adipose tissue. The determination that a particular agent substantially inhibits only a specific target or only a target in a specific tissue may readily be made by using or adapting routine procedures. One suitable assay measures activity of the target (such as PKC-δ) in the tissues of interest (such as liver, muscle, and adipose tissue), for example as described in Example 1, below.

Subject: A living multi-cellular vertebrate organism, a category that includes both human and non-human mammals.

Therapeutically Effective Amount: An amount or dose sufficient to prevent advancement, or to cause regression of a disease or syndrome or is capable of relieving symptoms of a disease or syndrome (such as obesity, metabolic syndrome, and/or diabetes).

Thio-Gold Compound: A family of organo-gold compounds that include a gold atom linked to at least one functional group via a thiol bond. In some examples, thio-gold compounds may exist as polymers with Au—S—Au—S chains with functional groups (such as malate or glucose groups) attached to the sulfur atoms. In some non-limiting examples, a thio-gold compound includes aurothiomalate (such as sodium ATM or disodium ATM), aurothioglucose, or auranofin.

Treating or Inhibiting a Disease: "Treating" a disease, disorder, or condition refers to a therapeutic intervention that ameliorates a sign or symptom of a disease or pathological condition (such as obesity, metabolic syndrome, or diabetes) after it has begun to develop. "Inhibiting" a disease or disorder refers to inhibiting the full development of a disease, for example in a person who is known to have a disease or pathological condition or be at risk for developing a disease, such as obesity, metabolic syndrome, or diabetes. Inhibition of a disease can span the spectrum from partial inhibition to substantially complete inhibition (prevention) of the disease. In some examples, the term "inhibiting" refers to reducing or delaying the onset or progression of a disease or disorder. In other examples, "inhibiting" a disease refers to lessening symptoms of the disease or disorder. A subject to be administered with a therapeutically effective amount of the pharmaceutical compound to inhibit or treat the above illnesses can be identified by standard diagnosing techniques for such a disorder.

III. Methods of Treating Obesity, Metabolic Syndrome, and Diabetes

Disclosed herein are methods for treating or inhibiting obesity, metabolic syndrome, diabetes, or a combination of these conditions. The methods include selecting a subject with obesity, metabolic syndrome, or diabetes (for example, type 1 or type 2 diabetes) and administering to the subject a therapeutically effective amount of a composition comprising a compound that specifically inhibits hepatic protein kinase C $(PKC)_{-\iota}$, thereby treating the obesity, metabolic syndrome, or diabetes in the subject.

In some examples, the methods include selecting a subject with obesity. In other examples, the methods include selecting a subject with metabolic syndrome. In further examples, the methods include selecting a subject with diabetes (such as type II diabetes). The selected subject may have a combination of two of obesity, metabolic syndrome, and diabetes, or may also have all three conditions. Methods of identifying a subject with each of these conditions are discussed below. In some examples, the selected subject does not have a neoplasm (for example, cancer) and/or the subject does not have rheumatoid arthritis.

The disclosed methods treat (for example, inhibit, or even prevent) obesity, metabolic syndrome, and/or diabetes, for example by increasing glucose tolerance, decreasing insulin resistance, decreasing serum triglycerides, decreasing serum free fatty acid levels, decreasing total serum cholesterol, decreasing serum low-density lipoprotein, increasing serum high-density lipoprotein, decreasing HbA1c levels, decreasing body weight, decreasing hepatosteatosis, or a combination of two or more thereof in the subject, for example as compared to a control. In some examples, the disclosed methods also include treating or inhibiting individual features of metabolic syndrome (such as elevated serum triglycerides, free fatty acids, and/or total cholesterol, or hepatosteatosis) in a subject with or without metabolic syndrome.

The disclosed methods utilize compositions including a compound that specifically inhibits hepatic $PKC_{-\iota}$. In specific examples, the compound does not substantially inhibit $PKC_{-\iota}$ in muscle or adipose tissue. In some examples the compound inhibits basal and/or insulin-stimulated $PKC_{-\iota}$ activity in hepatic tissue (for example, in hepatocytes) by at least 10% (such as at least 15%, 20%, 25%, 30%, 40%, 50%, 60%, 70%, 80%, 90%, 95%, or more) as compared to hepatic $PKC_{-\iota}$ activity in the absence of the compound. In further examples, the compound inhibits basal and/or insulin-stimulated $PKC_{-\iota}$ activity in muscle or adipose tissue by less than 10% (such as 9%, 8%, 7%, 6%, 5%, 4%, 3%, 2%, 1%, or less) as compared to muscle or adipose PKC$_{-\iota}$ activity in the absence of the compound. In some examples, the compound is not a protein or a nucleic acid.

In some embodiments the compound that specifically inhibits hepatic PKC$_{-\iota}$ includes a thio-gold compound. Thiogold compounds are a family of compounds that include a gold atom linked to at least one functional group via a thiol bond. Thio-gold compounds are well known in the art (see, e.g., Kean and Hogan, *Singapore Medical Journal* 28:110-116, 1987; incorporated herein by reference). In some examples, thio-gold compounds exist as polymers with Au—S—Au—S chains with functional groups (such as malate or glucose groups) attached to the sulfur atoms. Thiogold compounds may have a general structure as follows:

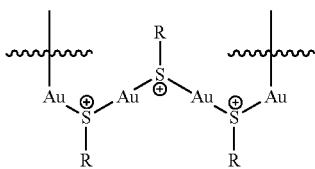

In non-limiting examples, R is be malate or glucose. The thio-gold compound (in polymeric form) may include at least 2 gold atoms (such as 2, 3, 4, 5, 6, 7, 8, 9, 10, or more gold atoms). In some examples, the thio-gold compound is a pharmaceutically acceptable salt, for example, a sodium or disodium salt.

In some non-limiting examples, the thio-gold compound is aurothiomalate (ATM; e.g., MYOCRISIN® or MYOCHRISINE®), aurothioglucose (ATG; e.g., SOLGANAL®), or auranofin (e.g., RIDAURA®). The disclosed methods also include derivatives of thio-gold compounds (such as derivatives of ATM, ATG, or auranofin). Exemplary aurothiomalate compounds and related compounds and compositions and methods for their production are described in U.S. Pat. Nos. 1,994,213; 2,352.124; 2,509,200; 3,792,165; 4,165,380; 4,330,530; and 4,599,436; each of which is incorporated herein by reference in its entirety. Exemplary auranofin compounds and related compounds and compositions and methods for their production are described in U.S. Pat. Nos. 3,635, 945; 4,125,710; 4,125,711; 4,115,642; and 4,131,732; each of which is incorporated herein by reference in its entirety.

In other embodiments, the compound that specifically inhibits hepatic PKC$_{-\iota}$ includes 1H-imidazole-4-carboxamide 5-amino-1-[2,3-dihydroxy-4-[(phosphonooxy)methyl] cyclopentyl]-[1R-(1α,2β,3β,4α)] (ICAPP) or a derivative thereof. ICAPP has the structure:

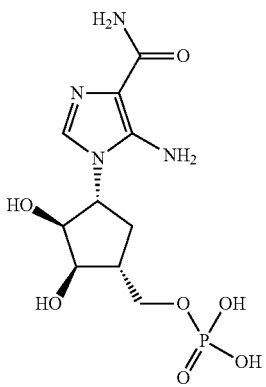 [SMILES: NC(=O)c1ncn([C@@H]2C[C@H](COP(=O)(O)O)[C@@H](O)[C@H]2O)c1N]

In some examples, ICAPP or the derivative thereof is a pharmaceutically acceptable salt.

Compounds for use in the disclosed methods also include derivatives of the compounds described above. Methods for synthesis of derivative compounds are known to those of skill in the art. For instance, the use of derivatives of ICAPP is contemplated. In one example, derivatives of ICAPP include, but are not limited to compounds wherein the imidazole and/ or carboxamide groups are modified or replaced. In particular examples, derivatives of ICAPP retain the phosphate and cyclopentyl moieties of ICAPP. In some examples, a derivative of ICAPP includes substitution of one or more —OH groups with a lower alkyl group (for example, a hydrocarbon group having a cyclic, branched or unbranched saturated carbon chain containing 1 to 10 carbon atoms). In a particular example, a derivative of ICAPP includes the dephosphorylated form of ICAPP or the dephosphorylated form of a derivative of ICAPP. In one example, the derivative is ICAP (1H-imidazole-4-carboxamide 5-amino-1-[2,3-dihydroxy-4-[hydroxymethyl]cyclopentyl]-[1R-(1α,2β,3β,4α)]), which can be phosphorylated in liver and other mammalian tissues to form ICAPP. ICAP has the structure:

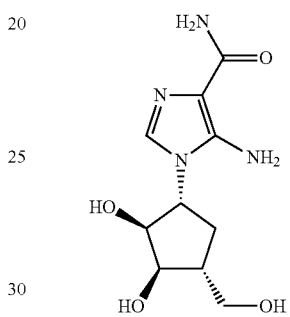

It is to be understood that hepatic PKC$_{-\iota}$ inhibitors for use in the present disclosure also include novel hepatic PKC$_{-\iota}$ inhibitors developed in the future. One of skill in the art can identify additional compounds that are inhibitors of PKC$_{-\iota}$, for example a compound that specifically inhibits hepatic PKC$_{-\iota}$. For example, methods of screening for inhibitors of PKC$_{-\iota}$ are known in the art (e.g., Stallings-Mann et al., *Cancer Res.* 66:1767-1774, 2006; incorporated herein by reference). The ability of a compound to specifically inhibit hepatic PKC$_{-\iota}$ can be assessed by measuring PKC$_{-\iota}$ activity in the presence and absence of a compound in hepatocytes, muscle, and adipose tissue or cells, for example as described in Example 1, below.

A. Metabolic Syndrome

In some embodiments, the disclosed methods include treating a subject with metabolic syndrome (for example, treating or inhibiting metabolic syndrome in the subject). Metabolic syndrome (sometimes referred to as Syndrome X, insulin resistance syndrome, or CHAOS) is a group of metabolic risk factors, including abdominal obesity, atherogenic dyslipidemia, elevated blood pressure, insulin resistance, prothrombotic state, and proinflammatory state, which correlate with increased risk of coronary heart disease, stroke, and type 2 diabetes. As much as 20-25% of the adult population worldwide is estimated to have metabolic syndrome.

There are a number of different guidelines for diagnosing metabolic syndrome. In one example, metabolic syndrome is diagnosed using the National Cholesterol Education Program Adult Treatment Panel III (NCEP ATPIII) criteria, which include at least three of central obesity (waist circumference ≥40 inches (male) or ≥36 inches (female)), triglycerides ≥1.7 mM (150 mg/dL), high density lipoprotein (HDL)<40 mg/dL (male) or <50 mg/dL (female), blood pressure ≥130/85 mm Hg, and fasting plasma glucose ≥6.1 mM (110 mg/dL). In another example, metabolic syndrome is diagnosed using the International Diabetes Federation criteria, which include central obesity (waist circumference based on ethnic specific values or body mass index >30 kg/m$^2$) and any two of triglycerides of ≥150 mg/dL or specific treatment for this lipid abnormality, HDL <40 mg/dL (male) or <50 mg/dL (female) or specific treatment for this lipid abnormality, systolic blood pressure ≥135 mm Hg or diastolic blood pressure ≥85 mm Hg or treatment of previously diagnosed hypertension, and fasting plasma glucose ≥100 mg/dL or previously diagnosed type 2 diabetes. See, e.g., Expert Panel on Detection, Evaluation, and Treatment of High Blood Cholesterol in Adults, *J. Am. Med. Assn.* 285:2486-2497, 2001; Alberti et al., *Diabet. Med.* 23:469-480, 2006. Other criteria for diagnosing metabolic syndrome include those from the European Group for the Study of Insulin Resistance, the World Health Organization, and the American Heart Association (e.g., Grundy et al., *Circulation* 109:433-438, 2004; Alberti et al., *Diabet. Med.* 15:539-553, 1998; Balkau and Charles, *Diabet. Med.* 16:442-443, 1999). One of skill in the art can utilize one or more of these guidelines to identify a subject with metabolic syndrome or at risk of developing metabolic syndrome.

In some embodiments, the disclosed methods include treating metabolic syndrome by decreasing triglyceride levels, decreasing total serum cholesterol, decreasing serum LDL levels, increasing serum HDL levels, decreasing blood pressure, decreasing fasting blood glucose, decreasing levels of markers of a prothrombotic state, decreasing levels of markers of a proinflammatory state, or decreasing levels of vascular adhesion molecules in a subject as compared with a control. In some examples, the method includes two or more (such as 3, 4, 5, 6, or 7) of decreasing triglyceride levels, decreasing total serum cholesterol, decreasing serum LDL levels, increasing serum HDL levels, decreasing blood pressure, decreasing fasting blood glucose, decreasing levels of markers of a prothrombotic state, decreasing levels of markers of a proinflammatory state, or decreasing levels of vascular adhesion molecules in a subject as compared with a control.

In some examples, administration of a compound that specifically inhibits hepatic PKC$_{-\iota}$ (including but not limited to ATM or ICAPP or derivatives thereof) treats metabolic syndrome by decreasing triglyceride levels in a subject, for example decreasing triglyceride levels by at least 5% (such as at least 10%, 15%, 20%, 25%, 30%, 35%, or more) as compared with a control. In some examples, the method includes decreasing triglyceride levels in a subject to <150 mg/dL. Methods of determining triglyceride levels in a subject (for example in a blood sample from a subject) are routine. In further examples, administration of a compound that specifically inhibits hepatic PKC$_{-\iota}$ treats metabolic syndrome by increasing HDL levels in a subject, for example, increasing HDL levels by at least 5% (such as at least 10%, 15%, 20%, 25%, 30%, 35%, or more) as compared with a control. In some examples, the method includes increasing HDL levels in a male subject to ≥40 mg/dL or increasing HDL levels in a female subject to ≥50 mg/dL. Methods of determining HDL levels in a subject (for example, in a blood sample from a subject) are routine. In still further examples, administration of a compound that specifically inhibits hepatic PKC$_{-\iota}$ treats metabolic syndrome by decreasing LDL levels in a subject, for example, for example decreasing LDL levels by at least 5% (such as at least 10%, 15%, 20%, 25%, 30%, 35%, or more) as compared with a control. In some examples, the method includes decreasing LDL levels in a subject to <130 mg/dL. Methods of determining LDL levels in a subject (for example in a blood sample from a subject) are routine. In additional examples, administration of a compound that specifically inhibits hepatic PKC$_{-\iota}$ (including but not limited to ATM or ICAPP or a derivative thereof) treats metabolic syndrome by decreasing blood pressure in a subject, for example, decreasing blood pressure (such as systolic pressure, diastolic pressure, or both) by at least 5% (such as at least 10%, 15%, 20%, 25%, 30%, 35%, or more) as compared with a control. In some examples, the method includes decreasing blood pressure in the subject to <135/85 mm Hg or decreasing systolic blood pressure to <135 mm Hg or diastolic blood pressure to <85 mm Hg.

In further examples, administration of a compound that specifically inhibits hepatic PKC$_{-\iota}$ (including but not limited to ATM or ICAPP) treats metabolic syndrome by decreasing blood glucose levels (such as fasting plasma glucose (FPG)) in a subject, for example, decreasing blood glucose by at least 5% (such as at least 10%, 15%, 20%, 25%, 30%, 35%, or more) as compared with a control. In some examples, the method includes decreasing FPG to <110 mg/dL. Methods to measure blood glucose levels in a subject (for example, in a blood sample from a subject) are routine. In still further examples, administration of a compound that specifically inhibits hepatic PKC$_{-\iota}$ (including but not limited to ATM or ICAPP or a derivative thereof) treats metabolic syndrome by decreasing markers of a prothrombotic state (such as plasminogen activator inhibitor-1 (PAI-1) or fibrinogen) in a subject, for example, decreasing levels of PAI-1 and/or fibrinogen by at least 5% (such as at least 10%, 15%, 20%, 25%, 30%, 35%, or more) as compared with a control. In additional examples, administration of a compound that specifically inhibits hepatic PKC$_{-\iota}$ treats metabolic syndrome by decreasing markers of a proinflammatory state (such as C-reactive protein (CRP), serum amyloid A protein, or homocysteine) in a subject, for example decreasing levels of CRP, serum amyloid A protein, and/or homocysteine by at least 5% (such as at least 10%, 15%, 20%, 25%, 30%, 35%, or more) as compared with a control. In further examples, administration of a compound that specifically inhibits hepatic PKC$_{-\iota}$ treats metabolic syndrome by decreasing vascular adhesion molecules (such as vascular cell adhesion molecule (VCAM), intracellular adhesion molecule (ICAM), or E-selectin) in a subject, for example, decreasing levels of VCAM, ICAM, or E-selection by at least 5% (such as at least 10%, 15%, 20%, 25%, 30%, 35%, or more) as compared with a control. Levels of prothrombotic, proinflammatory, or vascular adhesion molecules in a subject (for example, in a blood sample from a subject) can be determined by routine methods, such as immunoassay (for example, by ELISA).

B. Diabetes

In some embodiments, the disclosed methods include treating a subject with diabetes (such as pre-diabetes, type 1 diabetes or type 2 diabetes), for example, treating or inhibiting diabetes in the subject. In some examples, a subject with diabetes has insulin resistance. Diabetes may be clinically diagnosed by a fasting plasma glucose (FPG) concentration of greater than or equal to 7.0 mmol/L (126 mg/dL), or a plasma glucose concentration of greater than or equal to 11.1 mmol/L (200 mg/dL) at about two hours after an oral glucose tolerance test (OGTT) with a 75 g load. A more detailed description of diabetes may be found in *Cecil Textbook of Medicine*, J. B. Wyngaarden, et al., eds. (W.B. Saunders Co., Philadelphia, 1992, 19$^{th}$ ed.). One of skill in the art can identify a subject with diabetes or at risk of developing diabetes (such as a subject with pre-diabetes).

In some embodiments, the disclosed methods treat diabetes by decreasing or improving insulin resistance in a subject. Insulin resistance is a decreased sensitivity or responsiveness to the metabolic actions of insulin. In some examples, insulin resistance results in increased blood glucose and/or increased blood insulin levels (such as fasting blood glucose or fasting blood insulin levels).

In some examples, insulin resistance is determined by hyperinsulinemic euglycemic clamp (glucose clamp), which measures the amount of glucose necessary to compensate for increased insulin levels without causing hypoglycemia (see, e.g., DeFronzo et al., *Am. J. Physiol.* 237:E214-E223, 1979). In one example, the glucose clamp method includes infusing insulin in a subject at 10-120 mU/m$^2$/min and infusing 20% glucose to maintain blood glucose levels between about 90-100 mg/dL. If low levels of glucose (such as ≤4 mg/min) are required to maintain blood glucose levels, then the subject is considered insulin resistant. High levels of glucose (such as ≥7.5 mg/min) indicate that the subject is insulin sensitive, while between 4-7.5 mg/min of glucose is considered to indicate impaired glucose tolerance (IGT), which is an early sign of insulin resistance.

In some examples of the disclosed method, administration of a compound that specifically inhibits hepatic $PKC_{\text{-}\iota}$ (including but not limited to ATM or ICAPP or a derivative thereof) treats diabetes by increasing the amount of glucose required to maintain blood glucose levels in a glucose clamp in a subject, for example, by at least 5% (such as at least 10%, 15%, 20%, 25%, 30%, 35%, or more) as compared with a control. In some examples, the method includes increasing the amount of glucose required to maintain blood glucose levels in a glucose clamp to >4 mg/min glucose. In other examples, the method includes increasing the amount of glucose required to maintain blood glucose levels in a glucose clamp to ≥7.5 mg/min glucose.

In another example, insulin resistance is determined by the frequently sampled intravenous glucose tolerance test (FSIVGTT; Bergman, *Diabetes* 38:1512-1527, 1989). FSIVGTT is performed by administering intravenous glucose with frequent blood sampling to determine glucose and insulin levels. Insulin is injected 20 minutes after the start of glucose administration. The insulin sensitivity index (SI), reflecting increase in fractional glucose disappearance per unit of insulin increase, is calculated. In some examples, an SI value of ≤2 µU/min/mL indicates insulin resistance. In some examples of the disclosed method, administration of a compound that specifically inhibits hepatic $PKC_{\text{-}\iota}$ (including but not limited to ATM or ICAPP or a derivative thereof) treats diabetes by increasing the insulin sensitivity index of a subject, for example, by at least 5% (such as at least 10%, 15%, 20%, 25%, 30%, 35%, or more) as compared with a control. In some examples, the method includes increasing the insulin sensitivity index to >2 µU/min/mL.

In other examples, insulin resistance is determined by quantitative insulin sensitivity check index (QUICKI; Katz et al., *J. Clin. Endocrinol. Metab.* 85:2402-2410, 2000). QUICKI is calculated from fasting glucose and fasting insulin levels:

$$\text{QUICKI}=1/[(\log(I_0)+(\log(G_0)]$$

wherein $I_0$ is the fasting plasma insulin level (µU/mL) and $G_0$ is the fasting blood glucose level (mg/dL). In some examples of the disclosed method, administration of a compound that specifically inhibits hepatic $PKC_{\text{-}\iota}$ (including but not limited to ATM or ICAPP or a derivative thereof) treats diabetes by increasing the QUICKI value in a subject by at least 5% (such as at least 10%, 15%, 20%, 25%, 30%, 35%, or more) as compared with a control. In some examples, the method includes increasing the subject's QUICKI to >0.350.

In other examples, insulin resistance is determined by the homeostasis model assessment (HOMA-IR; Matthews et al., *Diabetologia* 28:412-429, 1985). HOMA-IR is calculated from fasting glucose and fasting insulin levels:

$$\text{HOMA-}IR=[\text{fasting plasma insulin}\times\text{fasting plasma glucose}]/22.5$$

wherein fasting plasma insulin is expressed as µU/mL and fasting plasma glucose is expressed as mM. In some examples of the disclosed method, administration of a compound that specifically inhibits hepatic $PKC_{\text{-}\iota}$ (including but not limited to ATM or ICAPP or a derivative thereof) treats diabetes by decreasing the HOMA-IR value in a subject by at least 5% (such as at least 10%, 15%, 20%, 25%, 30%, 35%, or more) as compared with a control. In some examples, the method includes decreasing HOMA-IR to ≤4.

In some examples, insulin resistance includes impaired glucose tolerance (IGT), alone or in combination with impaired fasting glucose regulation. An oral glucose tolerance test (OGTT) can be used to determine if a subject has IGT. An OGTT two-hour plasma glucose of greater than or equal to 140 mg/dL and less than 200 mg/dL (7.8-11.0 mM) is considered to be IGT.

In some examples, fasting plasma glucose (FPG) of greater than about 100 mg/dL and less than 126 mg/dL (5.6-6.9 mM) indicates that a subject has impaired fasting glucose regulation or insulin resistance. In some examples, administration of a compound that specifically inhibits hepatic $PKC_{\text{-}\iota}$ treats diabetes by decreasing plasma glucose levels (such as FPG or 2-hour glucose levels following oral glucose tolerance test (OGTT)) in a subject, for example, decreasing plasma glucose levels by at least 5% (such as at least 10%, 15%, 20%, 25%, 30%, 35%, or more) as compared with a control. In some examples, the method includes decreasing FPG to <110 mg/dL or <100 mg/dL. Methods to measure plasma glucose in a subject (for example, in a blood sample from a subject) are routine, for example utilizing the glucose oxidase method.

In additional examples, a compound that specifically inhibits hepatic $PKC_{\text{-}\iota}$ (including but not limited to ATM or ICAPP or a derivative thereof) treats diabetes by decreasing plasma insulin levels (such as fasting plasma insulin or 2-hour insulin levels following OGTT) in a subject, for example, decreasing plasma insulin levels by at least 5% (such as at least 10%, 15%, 20%, 25%, 30%, 35%, or more) as compared with a control. In some examples, the method includes decreasing fasting plasma insulin levels to <15 µU/mL. Methods to measure plasma insulin in a subject (for example, in a blood sample from a subject), such as immunoassays, are routine.

In additional examples, a compound that specifically inhibits hepatic $PKC_{\text{-}\iota}$ treats diabetes by decreasing hemoglobin A1c (HbA1c) levels in the subject. HbA1c (glycated hemoglobin) is a form of hemoglobin formed by non-enzymatic glycation by exposure of hemoglobin to plasma glucose. As the average amount of plasma glucose increases, the fraction of glycated hemoglobin increases. Thus HbA1c level is a marker for average blood glucose levels over time (such as weeks or months) and is an indicator of glycemic control in a subject. In some examples, administration of a compound that specifically inhibits hepatic $PKC_{\text{-}\iota}$ treats diabetes by decreasing HbA1c levels in a subject, for example decreasing HbA1c levels by at least 5% (such as at least 10%, 15%, 20%, 25%, 30%, 35%, or more) as compared with a control. In some examples, the method includes decreasing HbA1c levels in a subject to less 7% (such as 6.5%, 6%, 5.5%, 5%, or less). Methods of determining HbA1c levels in a subject (for example in a blood sample from a subject) are routine, for example, by HPLC or immunoassay.

One of skill in the art will recognize that because of a lack of standardized assays, interassay variability in insulin measurements can confound defining universal ranges for insulin resistance and insulin sensitivity. Therefore, in some examples, insulin sensitive subjects include the top $25^{th}$ percentile of insulin sensitive subjects in a given cohort where insulin levels are measured in the same central reference laboratory. Similarly, in some examples, insulin resistant subjects include the bottom $25^{th}$ percentile of insulin sensitive subjects in a given cohort where insulin levels are measured in the same central reference laboratory. In additional examples, impaired glucose tolerance can be defined according the results of an oral glucose tolerance test using guidelines that are published by the American Diabetes Association. See, e.g., *Diabetes Care* 33:S62-S69, 2010.

C. Obesity

In some embodiments, the disclosed methods include treating a subject with obesity, for example treating or inhibiting obesity or overweight in the subject. In some examples, the method includes selecting a subject with obesity (such as an overweight or obese subject). A subject may be considered overweight or obese if their BMI is greater than 25 kg/m$^2$, their waist circumference is greater than 35 inches (female) or 40 inches (male) or body fat percentage is greater than 25% (male) or 32% (female). In some examples, treating obesity includes decreasing body weight, such as one or more of decreasing total body weight, decreasing BMI, decreasing waist circumference, and decreasing body fat (such as total body fat, subcutaneous body fat, or visceral body fat).

In some examples, a compound that specifically inhibits hepatic PKC$_{-\iota}$ (including but not limited to ATM or ICAPP or a derivative thereof) treats obesity by reducing total body weight of the subject by at least about 1% (such as at least about 2%, 3%, 4%, 5%, 6%, 7%, 8%, 9%, 10%, 15%, 20%, 25%, or more). In particular examples, reduction in total body weight is determined relative to the starting total body weight of the subject (for example, prior to treatment with a hepatic PKC$_{-\iota}$ inhibitor).

In other examples, a compound that specifically inhibits hepatic PKC$_{-\iota}$ (including but not limited to ATM or ICAPP or a derivative thereof) treats obesity by decreasing BMI of the subject by at least about 1% (such as at least about 2%, 3%, 4%, 5%, 6%, 7%, 8%, 9%, 10%, 15%, 20%, 25%, or more). BMI is calculated by dividing weight (in kg) by height$^2$ (in meters$^2$). The current standards for both men and women accepted as "normal" are a BMI of 20-24.9 kg/m$^2$. In one embodiment, a BMI of greater than 25 kg/m$^2$ can be used to identify an obese subject. Grade I obesity (also called "overweight") corresponds to a BMI of 25-29.9 kg/m$^2$. Grade II obesity corresponds to a BMI of 30-40 kg/m$^2$; and Grade III obesity corresponds to a BMI greater than 40 kg/m$^2$. In particular examples, reduction in BMI is determined relative to the starting BMI of the subject (for example, prior to treatment with a hepatic PKC$_{-\iota}$ inhibitor). In other examples, decreasing BMI of a subject includes reduction of BMI from a starting point (for example BMI greater than 30 kg/m$^2$) to a target level (for example, BMI less than 30 kg/m$^2$, 29 kg/m$^2$, 28 kg/m$^2$, 27 kg/m$^2$, 26 kg/m$^2$, or 25 kg/m$^2$).

In further examples, a compound that specifically inhibits hepatic PKC$_{-\iota}$ (including but not limited to ATM or ICAPP or a derivative thereof) treats obesity by decreasing waist circumference by at least 1% (such as at least about 2%, 3%, 4%, 5%, 6%, 7%, 8%, 9%, 10%, 15%, 20%, 25%, or more). In particular examples, reduction in waist circumference is determined relative to the starting waist circumference of the subject (for example, prior to treatment with a hepatic PKC$_{-\iota}$ inhibitor). In other examples, decreasing waist circumference of a subject includes reduction of waist circumference from a starting point (for example greater than 40 inches for men or greater than 35 inches for women) to a target level (for example, waist circumference less than 40 inches for men or less than 35 inches for women).

In additional examples, a compound that specifically inhibits hepatic PKC$_{-\iota}$ (including but not limited to ATM or ICAPP or a derivative thereof) treats obesity by decreasing body fat (such as total body fat, subcutaneous body fat, or visceral body fat) of the subject by at least 1% (such as at least about 2%, 3%, 4%, 5%, 6%, 7%, 8%, 9%, 10%, 15%, 20%, 25%, or more). Methods of determining body fat (such as body fat percentage) are known to one of skill in the art. Such methods include near-infrared interactance, dual energy X-ray absorptiometry, body average density measurement, bioelectrical impedance analysis, skinfold tests (for example, Durnin-Womersley skinfold method or Jackson-Pollock skinfold method), and U.S. Navy circumference method. In particular examples, reduction in body fat is determined relative to the starting body fat of the subject (for example, prior to treatment with a hepatic PCK-$\iota$ inhibitor). In other examples, decreasing body fat of a subject includes reduction of body fat from a starting point (for example greater than about 25% body fat for men or greater than about 32% body fat for women) to a target level (for example, body fat of less than about 25% for men or less than about 32% for women). In some examples, a target body fat level may be about 14-24% body fat for men or about 21-31% body fat for women.

D Controls

In some embodiments, the disclosed methods include comparing one or more indicator of metabolic syndrome (such as triglyceride levels, HDL levels, blood pressure, blood glucose levels, or levels of one or more markers of a prothrombotic state, a proinflammatory state or vascular adhesion) to a control, wherein an increase or decrease in the particular indicator relative to the control (as discussed above) indicates effective treatment of the metabolic syndrome. In other embodiments, the disclosed methods include comparing one or more indicator of diabetes or insulin resistance (such as blood glucose levels, blood insulin levels, insulin sensitivity index, HOMA-IR, or QUICKI) to a control, wherein an increase or decrease in the particular indicator relative to the control (as discussed above) indicates effective treatment of insulin resistance. In further embodiments, the disclosed methods include comparing one or more indicator of obesity (such as body weight, BMI, waist circumference, or body fat) to a control, wherein an increase or decrease in the particular indicator relative to the control (as discussed above) indicates effective treatment of obesity.

The control can be any suitable control against which to compare the indicator of metabolic syndrome, diabetes, insulin resistance, or obesity in a subject. In some embodiments, the control is a sample obtained from a healthy subject (such as a subject without metabolic syndrome, diabetes, or obesity). In some embodiments, the control is a historical control or standard reference value or range of values (such as a previously tested control sample, such as a group of subjects with metabolic syndrome obesity or diabetes, or group of samples from subjects that do not have metabolic syndrome obesity, or diabetes). In further examples, the control is a reference value, such as a standard value obtained from a population of normal individuals that is used by those of skill in the art. Similar to a control population, the value of the sample from the subject can be compared to the mean reference value or to a range of reference values (such as the high and low values in the reference group or the 95% confidence interval). In other examples, the control is the subject (or group of subjects) treated with placebo compared to the same subject (or group of subjects) treated with the therapeutic compound in a cross-over study. In further examples, the control may be the same subject or group of subjects prior to treatment.

IV. Pharmaceutical Compositions and Administration

Pharmaceutical compositions that include a compound that specifically inhibits hepatic $PKC_{-\iota}$ (including but not limited to ATM or ICAPP or a derivative thereof) can be formulated with an appropriate pharmaceutically acceptable carrier, depending upon the particular mode of administration chosen. In one example, the pharmaceutical composition includes a compound that specifically inhibits hepatic $PKC_{-\iota}$ and a pharmaceutically acceptable carrier. In some examples, the pharmaceutical composition consists essentially of a compound that specifically inhibits hepatic $PKC_{-\iota}$ and a pharmaceutically acceptable carrier.

The pharmaceutically acceptable carriers and excipients useful in this disclosure are conventional. See, e.g., *Remington: The Science and Practice of Pharmacy*, The University of the Sciences in Philadelphia, Editor, Lippincott, Williams, & Wilkins, Philadelphia, Pa., 21$^{st}$ Edition (2005). For instance, parenteral formulations usually comprise injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, other proteins, such as human serum albumin or plasma preparations. In some embodiments, the compound that specifically inhibits hepatic $PKC_{-\iota}$ is included in a controlled release formulation, for example, a microencapsulated formulation. Various types of biodegradable and biocompatible polymers, methods can be used, and methods of encapsulating a variety of synthetic compounds, proteins and nucleic acids, have been well described in the art (see, for example, U.S. Pat. Publication Nos. 2007/0148074; 2007/0092575; and 2006/0246139; U.S. Pat. Nos. 4,522,811; 5,753,234; and 7,081,489; PCT Publication No. WO/2006/052285; Benita, *Microencapsulation: Methods and Industrial Applications*, 2$^{nd}$ ed., CRC Press, 2006).

In other examples, the compound that specifically inhibits hepatic $PKC_{-\iota}$ is included in a nanodispersion system. Nanodispersion systems and methods for producing such nanodispersions are well known to one of skill in the art. See, e.g., U.S. Pat. No. 6,780,324; U.S. Pat. Publication No. 2009/0175953. For example, a nanodispersion system includes a biologically active agent and a dispersing agent (such as a polymer, copolymer, or low molecular weight surfactant). Exemplary polymers or copolymers include polyvinylpyrrolidone (PVP), poly(D,L-lactic acid) (PLA), poly(D,L-lactic-co-glycolic acid (PLGA), poly(ethylene glycol). Exemplary low molecular weight surfactants include sodium dodecyl sulfate, hexadecyl pyridinium chloride, polysorbates, sorbitans, poly(oxyethylene)alkyl ethers, poly(oxyethylene)alkyl esters, and combinations thereof. In one example, the nanodispersion system includes PVP and a compound that specifically inhibits hepatic $PKC_{-\iota}$ (such as 80/20 w/w). In some examples, the nanodispersion is prepared using the solvent evaporation method. See, e.g., Kanaze et al., *Drug Dev. Indus. Pharm.* 36:292-301, 2010; Kanaze et al., *J. Appl. Polymer Sci.* 102:460-471, 2006.

In some examples, the compound that specifically inhibits hepatic $PKC_{-\iota}$ includes pharmaceutically acceptable salts of such compounds. "Pharmaceutically acceptable salts" of the presently disclosed compounds include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Description of suitable pharmaceutically acceptable salts can be found in *Handbook of Pharmaceutical Salts, Properties, Selection and Use*, Wiley VCH (2002).

In some examples, the pharmaceutical compositions disclosed herein comprise a compound that specifically inhibits hepatic $PKC_{-\iota}$ and at least one pharmaceutically acceptable carrier. In other examples, the composition consists essentially of a compound that specifically inhibits hepatic $PKC_{-\iota}$ and at least one pharmaceutically acceptable carrier. In the present disclosure, "consists essentially of" indicates that additional active compounds (for example additional inhibitors of hepatic $PKC_{-\iota}$) are not included in the composition, but that other inert agents (such as fillers, wetting agents, or the like) can be included, and "consists of" indicates that additional agents are not included in the composition.

The dosage form of the pharmaceutical composition will be determined by the mode of administration chosen. For instance, in addition to injectable fluids, topical, inhalation, oral and suppository formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, cellulose, starch, or magnesium stearate. Actual methods of preparing such dosage forms are known, or will be apparent, to those skilled in the art.

The pharmaceutical compositions that include a compound that specifically inhibits hepatic $PKC_{-\iota}$ (such as ICAPP or ICAP) can be formulated in unit dosage form, suitable for individual administration of precise dosages. In one specific, non-limiting example, a unit dosage contains from about 0.1 mg to about 1 g of a compound that specifically inhibits hepatic $PKC_{-\iota}$ (such as about 0.1 to about 10 mg, about 1 mg to about 100 mg, about 10 mg to about 500 mg, about 25 mg to about 250 mg, or about 50 mg to about 100 mg, for example about 0.1 mg, 1 mg, 5 mg, 10 mg, 20 mg, or 50 mg). The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The compositions of this disclosure including a compound that specifically inhibits hepatic $PKC_{-\iota}$ can be administered to humans or other animals on whose tissues they are effective in various manners such as orally, intravenously, intramuscularly, intraperitoneally, intranasally, intradermally, intrathecally, subcutaneously, via inhalation, or via suppository. In one non-limiting example, the composition is administered subcutaneously. In other examples, the composition is administered intramuscularly. In some examples, the composition is administered orally. The particular mode of administration and the dosage regimen will be selected by the attending clinician, taking into account the particulars of the case (e.g. the subject, the disease state involved, the particular treatment, and whether the treatment is prophylactic). Treatment can involve daily or multi-daily doses of compound(s) over a period of a few days to months, or even years. In a particular non-limiting example, treatment involves once daily dose of a compound that specifically inhibits hepatic $PKC_{-\iota}$. In other examples, treatment involves once weekly administration of a compound that specifically inhibits $PKC_{-\iota}$.

In some examples, a therapeutically effective amount of a compound that specifically inhibits hepatic $PKC_{-\iota}$ is about 0.01 mg/kg to about 50 mg/kg (for example, about 0.1 mg/kg to about 10 mg/kg, about 0.25 mg/kg to about 2.5 mg/kg, or about 0.5 mg/kg to about 1 mg/kg). In one specific example, a therapeutically effective amount of a compound that specifically inhibits hepatic $PKC_{-\iota}$ is about 0.5 mg/kg to about 1 mg/kg of ATM. In another particular example, a therapeutically effective amount of a compound that specifically inhibits hepatic $PKC_{-\iota}$ includes about 0.1 mg/kg to about 10 mg/kg of ICAPP or ICAP (such as about 1 mg/kg ICAPP or ICAP). In another example, a therapeutically effective amount of a compound that specifically inhibits hepatic $PKC_{-\iota}$ includes about 0.1 mg to about 1 mg of ICAPP or ICAP.

A therapeutically effective amount of a compound that specifically inhibits hepatic $PKC_{-\iota}$ can be the amount of a compound that specifically inhibits hepatic $PKC_{-\iota}$ necessary to treat obesity, metabolic syndrome, and/or diabetes in a subject. A therapeutically effective amount of a compound that specifically inhibits hepatic $PKC_{-\iota}$ can be administered in a single dose, or in several doses, for example daily, every other day, every third day, every fourth day, every fifth day, every sixth day, or weekly during a course of treatment. However, the therapeutically effective amount will be dependent on the subject being treated, the severity and type of the affliction, and the manner of administration of the therapeutic(s).

The present disclosure also includes combinations of a compound that specifically inhibits hepatic $PKC_{-\iota}$ with one or more other therapies useful in the treatment of obesity, metabolic syndrome, or diabetes. For example, the compounds of this disclosure can be administered in combination with effective doses of antihyperglycemic agents (such as biguanides (for example, metformin) or sulfonylureas), insulin, glucagon-like peptide (GLP) or GLP analogs (such as exenatide or liraglutide), dipeptidyl peptidase-4 inhibitors (such as sitagliptin), thiazolidinediones (such as rosiglitazone, pioglitazone, troglitazone, rivoglitazone, or ciglitazone), lipid lowering compounds (such as statins or fibrates), or a combination of two or more thereof. In one particular example, ICAPP or ICAP is administered in combination with an effective dose of metformin. In another particular example, ICAPP or ICAP is administered in combination with an activator of AMP-activated protein kinase, such as 5-aminoimidazole 4-carboxamide riboside (AICAR). The term "administration in combination" or "co-administration" refers to both concurrent and sequential administration of the active agents. Administration of a compound that specifically inhibits hepatic $PKC_{-\iota}$ may also be provided in combination with lifestyle modifications, such as increased physical activity, caloric restriction, low fat diet, and/or smoking cessation.

A subject that has diabetes or a subject with insulin resistance (for example, a fasting plasma glucose of >100 mg/dL) is a candidate for treatment using the therapeutic methods disclosed herein. A subject with obesity (such as a subject in need of a reduction in body weight), for example, a subject with a body mass index of 25 kg/m² or more is a candidate for treatment using the therapeutic methods herein. A subject with metabolic syndrome (such as a subject with at least three of central obesity (waist circumference ≥40 inches (male) or ≥36 inches (female)), triglycerides ≥1.7 mM (150 mg/dL), high density lipoprotein (HDL)<40 mg/dL (male) or <50 mg/dL (female), blood pressure ≥130/85 mm Hg, and fasting plasma glucose ≥6.1 mM (110 mg/dL)) is also a candidate for treatment using the therapeutic methods disclosed herein. One of skill in the art can select appropriate subjects for treatment using the methods disclosed herein.

The following examples are provided to illustrate certain particular features and/or embodiments. These examples should not be construed to limit the disclosure to the particular features or embodiments described.

EXAMPLES

Example 1

Materials and Methods

Human Hepatocyte Incubations:

Human cryo-preserved hepatocytes (70-90% viability) were obtained from the Zen-Bio Corp (Research Triangle Park, North Carolina). These hepatocytes were harvested after perfusion with collagenase-containing buffer of livers surgically removed from non-diabetic patients (2 females and 6 males; ages, 43-60 years, 51±3 (mean±SEM); BMI, 23-35, 30±2) and T2DM patients (2 females and 3 males, ages, 46-68 years, 60±4; BMI, 27±2; all insulin-requiring) who had been maintained as transplant donors, but were ultimately rejected for administrative reasons. To maximize the importance of comparative differences, hepatocytes from T2DM and non-diabetic patients, and of similar age and sex, were routinely incubated and assayed side-by-side.

After thawing, the hepatocytes were distributed (approximately $10^6$ cells per 100 mm plate) and incubated approximately 16 hours overnight in Dulbecco's minimal essential medium containing 5% fetal calf serum, 100 units/ml sodium-penicillin, 100 µg/ml streptomycin-sulfate, 1 µM insulin and 2 µM dexamethasone. After washing, cells were incubated first for 2 hours in William's E medium (Sigma-Aldrich, St. Louis, Mo., catalog no. W1878) containing GLUTAMAX™ (Gibco/Invitrogen, Carlsbad, Calif.), 100 units/ml sodium-penicillin, 100 µg/ml streptomycin-sulfate, 10 µM insulin, 100 nM dexamethasone, and then for 2 hours in William's E medium containing 100 units/ml sodium penicillin, 100 µg/ml streptomycin-sulfate, 100 nM dexamethasone, 0.25 mg/ml transferrin, 0.25 µg/ml sodium selenite and 10 µM insulin. Cells were then washed and incubated for 3 hours in the same medium, but lacking insulin. Where indicated, an aPKC inhibitor was then added and incubation was continued for 30 min, after which, cells were treated either for 15 min with or without 100 nM insulin for acute signaling studies, or for 6 hours, with or without 1 µM insulin for expression studies. After incubation, cells were sonicated in homogenizing buffer.

Human Muscle Samples: Biopsies of vastus lateralis muscles were obtained from non-diabetic and T2DM humans during clamp studies as previously described (Beeson et al., *Diabetes* 52:1926-1934, 2003). All experimental procedures involving humans were approved by the Institutional Review Board of the University of South Florida College of Medicine, and the James A. Haley Veterans Administration Medical Center Research and Development Committee, Tampa, Fla., and conducted in accordance with the Declaration of Helsinki and Good Clinical Practice.

In Vivo Mouse Studies: Male wild type (WT) and heterozygous muscle-specific PKC-λ knockout (Het-MλKO) mice were generated as described (Farese et al., *J. Clin. Invest.* 117:2289-2301, 2007) and used at 6-12 months of age, when the O/MS/T2DM phenotype in MλKO mice is well-developed. Mice were housed in a temperature-controlled environment with alternating 12-hour light and dark cycles, and fed ad libitum with standard chow (Harlan Teklad 20/18 with 5% fat, (10% of calories from fat)). All experimental procedures in mice were approved by the Institutional Animal Care and Use Committees of the Roskamp Institute and the University of South Florida College of Medicine, and the James A. Haley Veterans Administration Medical Center Research and Development Committee, Tampa, Fla.

Where indicated, mice were injected subcutaneously (SC) once daily for 8 days with 0.2 ml vehicle or vehicle containing aPKC inhibitor, either: (a) aurothiomalate (ATM; MYOCHRISINE®, Taylor Pharmaceuticals, Buffalo Grove, Ill.) at 60 mg/kg body weight; this once daily dose was found to be maximally effective in studies of aPKC-dependent lung cancer progression (Fields et al., *Biochem. Soc. Trans.* 23:1996-2000, 2007); or (b) 1H-imidazole-4-carboxamide, 5-amino-1-[2,3-dihydroxy-4-[(phosphono-oxy)methyl]cyclopentyl-[1R-(1a,2b,3b,4a)] (ICAPP; prepared by Southern Research, Birmingham, Ala.) at 0.4 mg/kg body weight. On the morning of the eighth day of inhibitor treatment, mice were injected intraperitoneally (IP) with 0.9% saline or saline containing 1 U insulin/kg body weight 15 minutes before sacrifice, an optimal time for studies of insulin stimulation of aPKC and Akt in liver, muscle and adipose tissues (Standaert et al., *J. Biol. Chem.* 279:24929-24934, 2004; Sajan et al., *J. Lipid Res.* 50:1133-1145, 2009; Sajan et al., Diabetologia 52:1197-1207, 2009; Farese et al., *J. Clin. Invest.* 117:2289-2301, 2007). After killing, blood, liver, quadriceps muscle and abdominal adipose tissues were rapidly removed and homogenized in buffer with a POLYTRON® homogenizer.

Tissue and Immunoprecipitate Preparations: As previously described (Standaert et al., *J. Biol. Chem.* 279:24929-24934, 2004; Sajan et al., *J. Lipid Res.* 50:1133-1145, 2009; Sajan et al., *Diabetologia* 52:1197-1207, 2009; Farese et al., *J. Clin. Invest.* 117:2289-2301, 2007) hepatocytes and tissues from in vivo experiments were homogenized in ice-cold buffer containing 0.25 M sucrose, 20 mM Tris/HCl (pH 7.5), 2 mM EGTA, 2 mM EDTA, 1 mM phenylmethylsulfonyl fluoride (PMSF), 20 µg/ml leupeptin, 10 µg/ml aprotinin, 2 mM $Na_4P_2O_7$, 2 mM $Na_3VO_4$, 2 mM NaF, and 1 µM microcystin. After centrifugation for 10 minutes at 700×g to remove unbroken cells, debris, nuclei, and floating fat, cell lysates were stored at −70° C. After addition of 1% TRITON® X-100, 0.6% Nonidet and 150 mM NaCl, lysates were cleared of insoluble materials by low-speed centrifugation and subsequently immunoprecipitated with antibodies that target: (a) aPKCs (rabbit polyclonal antiserum from Santa Cruz Biotechnologies (Santa Cruz, Calif.) that recognizes C-termini of both PKC-λ and PKC-ζ); and (b) Akt2 (Upstate Cell Signaling/Millipore, Billerica, Mass.). Immunoprecipitates were collected on Sepharose-AG beads (Santa Cruz Biotechnologies).

aPKCι Assays: aPKC enzyme activity was measured as previously described (Standaert et al., *J. Biol. Chem.* 279: 24929-24934, 2004; Sajan et al., *J. Lipid Res.* 50:1133-1145, 2009; Sajan et al., *Diabetologia* 52:1197-1207, 2009; Farese et al., *J. Clin. Invest.* 117:2289-2301, 2007). In brief, aPKCs were immunoprecipitated from cell lysates with a rabbit polyclonal antiserum (Santa Cruz Biotechnologies) that recognizes the C-termini of both PKC-ζ and PKC-λ/ι (whereas mouse (Bandyopadhyay et al., *Endocrinol.* 141:4120-4127, 2000) and human (present findings) muscle contains mainly PKC-λ and PKC-ι, respectively, and little PKC-ζ, mouse and human liver contains substantial amounts of both PKC-ζ and PKC-λ (Sajan et al., *J. Lipid Res.* 50:1133-1145, 2009; Matsumoto et al., *J. Clin. Invest.* 112:935-944, 2003; and present results). Immunoprecipitates were collected on Sepharose-AG beads (Santa Cruz Biotechnologies), and beads were suspended and incubated for 8 minutes at 30° C. in 100 buffer containing 50 mM Tris/HCl (pH, 7.5), 100 µM $Na_3VO_4$, 100 µM $Na_4P_2O_7$, 1 mM NaF, 100 µM PMSF, 4 µg phosphatidylserine (Sigma-Aldrich), 50 µM [γ-$^{32}$P]ATP (NEN Life Science Products/Perkin-Elmer, Waltham, Mass.), 5 mM $MgCl_2$, and, as substrate, 40 µM serine analogue of the PKC-ε pseudosubstrate (BioSource/Invitrogen, Carlsbad, Calif.). After incubation, $^{32}$P-labeled substrate was trapped on P-81 filter paper and counted. This assay reflects the specific activity of a constant amount of aPKC (even in Het-MλKO mice) that is immunoprecipitated by supplier-prescribed amounts of antiserum (Farese et al., *J. Clin. Invest.* 117:2289-2301, 2007; Beeson et al., *Diabetes* 52:1926-1934, 2003).

In some cases, aPKC activation was assessed by immunoblotting for phosphorylation of the auto(trans)phosphorylation site, threonine-555 in PKC-ι and threonine-560 in PKC-ζ, which is both required for full activation and reflective of substrate phosphorylation (Farese and Sajan, *Am. J. Physiol. Endocrinol. Metab.* 298:E385-E394, 2010).

For assays of recombinant PKC-ι and PKC-ζ (10 ng/assay; Biovision, Mountain View, Calif.), 10 fM phosphatidylinositol-3,4,5-(PO_4)_3 (PIP_3; Matreya, Pleasant Gap, Pa.) ±1 ng phosphoinositide-dependent kinase-1 (PDK1; Upstate Cell Signaling) was added to maximally activate and thus better define aPKC activity.

Akt2 Assay: Akt2 enzyme activity was measured with a kit obtained from Upstate Cell Signaling, as described (Standaert et al., *J. Biol. Chem.* 279:24929-24934, 2004; Sajan et al., *J. Lipid Res.* 50:1133-1145, 2009; Sajan et al., Diabetologia 52:1197-1207, 2009; Farese et al., *J. Clin. Invest.* 117: 2289-2301, 2007). In brief, Akt2 was immunoprecipitated from lysates with rabbit polyclonal antibodies, collected on Sepharose-AG beads, and incubated as per kit directions. Akt1/2 activation was also assessed by immunoblotting for phosphorylation of serine-473.

Western Analyses: Western analyses were conducted as described (Standaert et al., *J. Biol. Chem.* 279:24929-24934, 2004; Sajan et al., *J. Lipid Res.* 50:1133-1145, 2009; Sajan et al., *Diabetologia* 52:1197-1207, 2009; Farese et al., *J. Clin. Invest.* 117:2289-2301, 2007), using the following antibodies/antisera for immunodetection after resolution of lysate proteins by SDS-PAGE: rabbit polyclonal anti-IRS-1 antiserum (Upstate Cell Signaling); rabbit polyclonal anti-IRS-2 antiserum (Santa Cruz Technologies); rabbit polyclonal anti-PKC-ζ/λ antiserum (Santa Cruz Biotechnologies); rabbit polyclonal anti-PKC-ζ antiserum (gift of Dr. Todd Sacktor); mouse monoclonal anti-PKC-ι/ζ antibodies (Transduction Laboratories/BD, East Rutherford, N.J.); rabbit polyclonal anti-Akt1/2 antiserum (Upstate Cell Signaling); rabbit polyclonal anti-phospho-serine -473-Akt1/2 antiserum (New England BioLabs, Beverly, Mass.): rabbit polyclonal antiphospho-threonine-410-PKC-α/-403-PKC-ι/λ antiserum (Upstate Cell Signaling); rabbit polyclonal anti-phospho-threonine-560-PKC-ζ/-555-PKC-ι/λ antiserum (Invitrogen); and anti-p65/RelA subunit of NFκB (Santa Cruz Biotechnologies). Samples from experimental groups were compared on the same blots, and corrected for recovery as needed by comparison to a housekeeping standard (glyceraldehyde-phosphate dehydrogenase (GAPDH); rabbit polyclonal antiserum; Santa Cruz Biotechnologies) that was not altered by T2DM or experimental treatments.

mRNA Measurements: As previously described (Sajan et al., *J. Lipid Res.* 50:1133-1145, 2009; Sajan et al., *Diabetologia* 52:1197-1207, 2009; Farese et al., *J. Clin. Invest.* 117: 2289-2301, 2007), tissues were added to TRIZOL® reagent (Invitrogen) and RNA was extracted and purified with the RNEASY® Mini-Kit (Qiagen; Valencia, Calif.) and RNAase-free DNAase set (Qiagen) as per kit instructions, quantified by measuring $A_{260}/A_{280}$, further checked for purity by electrophoresis on 1.2% agarose gels, and mRNA quantified by quantitative real-time reverse transcriptase-polymerase chain reaction (RT-PCR). Reverse transcription was accomplished with TAQMAN® reverse transcription reagent from Applied Biosystems (Foster City, Calif., USA). mRNAs were measured with a SYBR® Green kit (Applied Biosystems) using the nucleotide primers shown in Table 1.

TABLE 1

RT-PCR primers

| Gene | Primer Sequences | SEQ ID NO: |
|---|---|---|
| SREBP1c (mouse) | ATCGGCGCGGAAGCTGTCGGGGTAGCGTC (FOR) | 1 |
| | ACTGTCTTGGTTGATGAGCTGGAGCAT (REV) | 2 |
| FAS (mouse) | GAGGACACTCAAGTGGCTGA (FOR) | 3 |
| | GTGAGGTTGCTGTCGTCTGT (REV) | 4 |
| ACC (mouse) | GACTTCATGAATTTGCTGAT (FOR) | 5 |
| | AAGCTGAAAGCTTTCTGTCT (REV) | 6 |
| PEPCK (mouse) | GACAGCCTGCCCCAGGCAGTGA (FOR) | 7 |
| | CTGGCCACATCTCGAGGGTCAG (REV) | 8 |
| G6Pase (mouse) | TGCTGCTCACTTTCCCCACCAG (FOR) | 9 |
| | TCTCCAAAGTCCACAGGAGGT (REV) | 10 |
| IL-1β (mouse) | TTGACGGACCCCAAAAGATG (FOR) | 11 |
| | AGAAGGTGCTCATGTCCTCA (REV) | 12 |
| TNF-α (mouse) | ACGGCATGGATCTCAAAGAC (FOR) | 13 |
| | AGATAGCAAATCGGCTGACG (REV) | 14 |
| PKCζ (mouse) | CATGCAGAGGCAGAGAAAACT (FOR) | 15 |
| | TTAGGTCCCGGTAGATGATCC (REV) | 16 |
| PKCλ (mouse) | TCACTGACTACGGCATGTGTAA (FOR) | 17 |
| | CGCAGAAAGTGCTGGTTG (REV) | 18 |
| HPRT (mouse) | TGAAAGACTTGCTCGAGATGT (FOR) | 19 |
| | AAAGAACTTATAGCCCCCCTT (REV) | 20 |
| SREBP-1c (human) | CAGCCCCACTTCATCAAGG (FOR) | 21 |
| | ACTGTTGCCAAGATGGTTCCG (REV) | 22 |
| FAS (human) | TGTGGACATGGTCACGGAC (FOR) | 23 |
| | GGCATCAAACCTAGACAGGTC (REV) | 24 |
| ACC (human) | TCGCTTTGGGGGAAATAAAGTG (FOR) | 25 |
| | ACCACCTACGGATAGACCGC (REV) | 26 |
| PEPCK (human) | GCTCTGAGGAGGAGAATGG (FOR) | 27 |
| | TGCTCTTGGGTGACGATAAC (REV) | 28 |
| G6Pase (human) | GCTGAATGTCTGTCTGTCACGAA (FOR) | 29 |
| | GCAGAAGGACAAGACGTAGAAGA (REV) | 30 |
| IL-1β (human) | CAGGCCGCGTCAGTTGTTGT (FOR) | 31 |
| | CCGGAGCGTTGCAGTTCAGTG (REV) | 32 |
| TNF-α (human) | CGCCACCACGCTCTTCTG (FOR) | 33 |
| | ACGGCGATGCGGCTGATG (REV) | 34 |
| PKCζ (human) | CGGAACCCCGAATTACATC (FOR) | 35 |
| | ACCAGTCCACGCTGAACC (REV) | 36 |
| PKCι (human) | GGCTGCATTCTTGCTTTCA (FOR) | 37 |
| | TGTCGCTGCATATGAAACATT (REV) | 38 |
| HPRT (human) | CGTGATTAGTGATGATGAACCAG (FOR) | 39 |
| | CGAGCAAGACGTTCAGTCCT (REV) | 40 |

FOR, forward primer; REV, reverse primer; all sequences are 5'-3' orientation

Nuclear Preparations: As previously described (Sajan et al., *J. Lipid Res.* 50:1133-1145, 2009; Sajan et al., *Diabetologia* 52:1197-1207, 2009; Farese et al., *J. Clin. Invest.* 117: 2289-2301, 2007), liver nuclei were prepared with NE-PER® Nuclear and Cytoplasmic Extraction Reagents (Pierce Biotechnology/Thermo Scientific, Waltham, Mass.; Cat. No. 78833) Levels of the active p65/RelA subunit of NFκB were measured in these nuclear preparations.

Measurements of Serum Triglycerides, Cholesterol, Free Fatty Acids, Insulin and Glucose: Serum triglycerides, cholesterol, free fatty acids, insulin and glucose levels were measured as previously described (Sajan et al., *J. Lipid Res.* 50:1133-1145, 2009; Sajan et al., *Diabetologia* 52:1197-1207, 2009; Farese et al., *J. Clin. Invest.* 117:2289-2301, 2007).

Statistical Evaluations: Data are expressed as mean±standard error, and P values were determined by a one-way ANOVA and the least-significant multiple comparison method.

Example 2

Activity and Expression of aPKC in Human Hepatocytes and Muscle

This example describes the activity and expression of aPKC in hepatocytes and muscle from non-diabetic and T2DM humans.

Figure 2A:
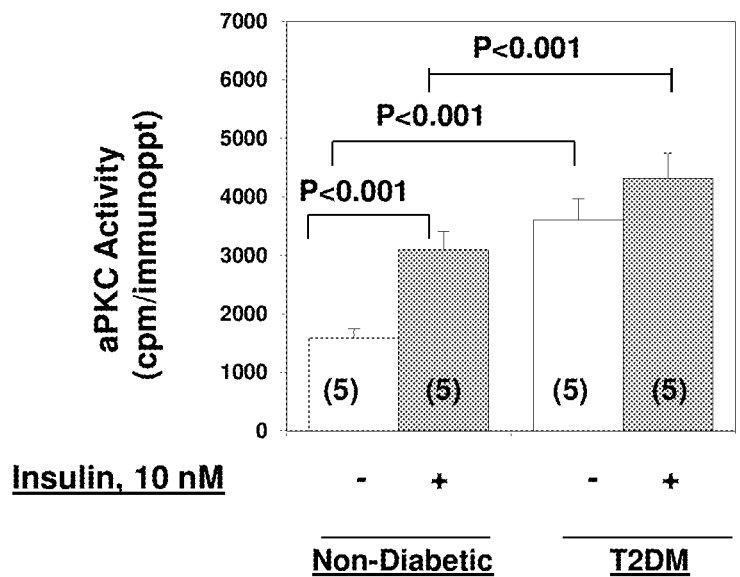
FIGS. 2A-C is a series of panels showing basal and insulin-stimulated aPKC and Akt in non-diabetic and T2DM human hepatocytes.
Figure 2B:
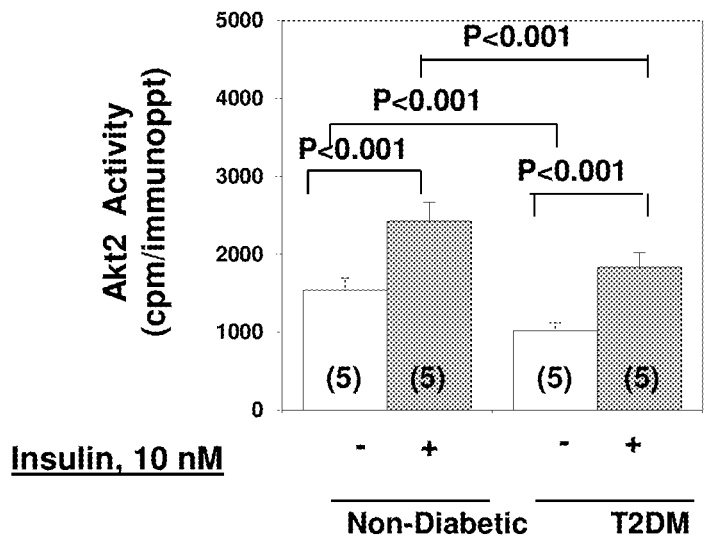

Activation of aPKC in Hepatocytes of Non-Diabetic and T2DM Humans:

Basal aPKC activity and acute (15-minute) activation of aPKC by insulin were not only conserved, but in fact significantly increased, in hepatocytes of T2DM humans, relative to non-diabetic hepatocytes (FIG. 2A). In marked contrast, basal and insulin-stimulated Akt2 activity was diminished (FIG. 2B) in T2DM relative to non-diabetic hepatocytes. Activities of aPKC and Akt2 were similarly altered in T2DM hepatocytes during 4-6-hour incubations in expression studies (FIGS. 2A and 2B). Also, aPKC auto(trans)phosphorylation (p-threonine-555/560-PKC-ι/ζ), which is essential for aPKC activation and reflective of substrate phosphorylation (Farese and Sajan, *Am. J. Physiol. Endocrinol. Metab.* 298: E385-E394, 2010), was: (a) increased basally in T2DM hepatocytes and by insulin in control hepatocytes (FIG. 2C); and (b) diminished by aPKC inhibitors (FIG. 3E).

Figure 2C:
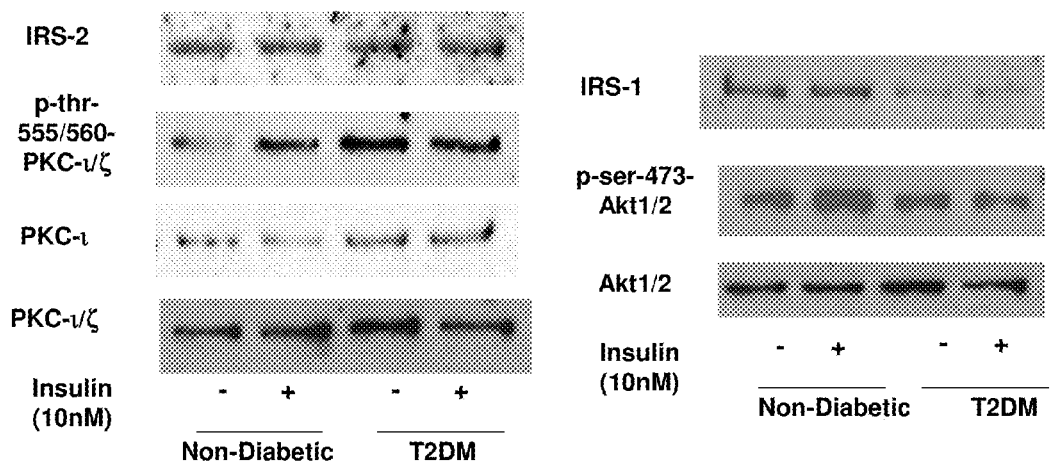
Figure 3A:
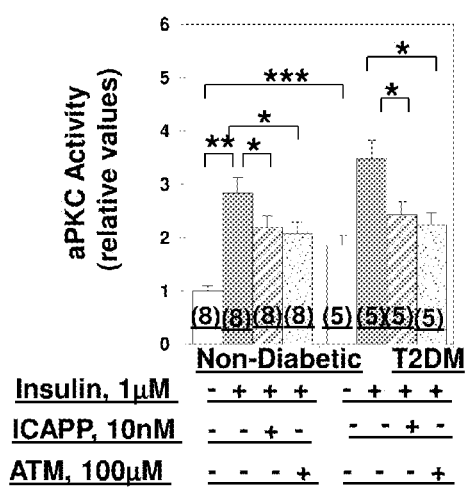
FIGS. 3A-L is a series of panels showing effects of the aPKC inhibitors, ICAPP and ATM in non-diabetic and T2DM hepatocytes.
Figure 3B:
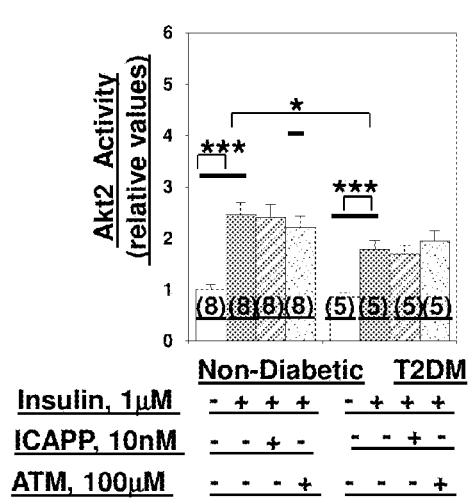
Figure 3C:
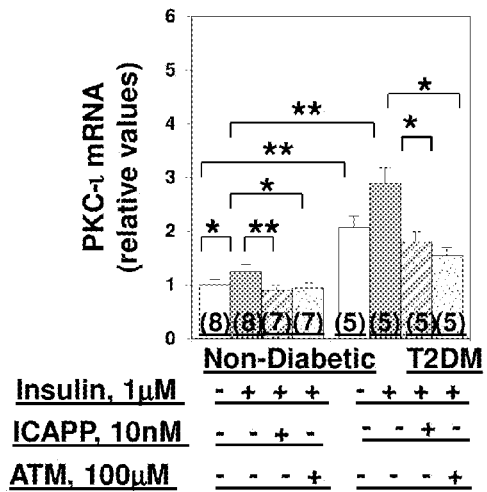

Expression of aPKC in Hepatocytes of Non-Diabetic and T2DM Humans:

Like aPKC enzyme activity, $PKC_{-\iota}$ expression was increased 2-fold in T2DM hepatocytes, relative to non-diabetic hepatocytes (FIG. 2C). Moreover, $PKC_{-\iota}$ expression in non-diabetic hepatocytes was increased modestly but significantly by 4-6-hour insulin treatment, and similar trends were seen in T2DM hepatocytes (FIG. 3C). Of further note, T2DM-induced and insulin-stimulated $PKC_{-\iota}$ expression was diminished by $PKC_{-\iota}$ inhibitors in non-diabetic and T2DM hepatocytes (FIG. 3C).

Figure 3D:
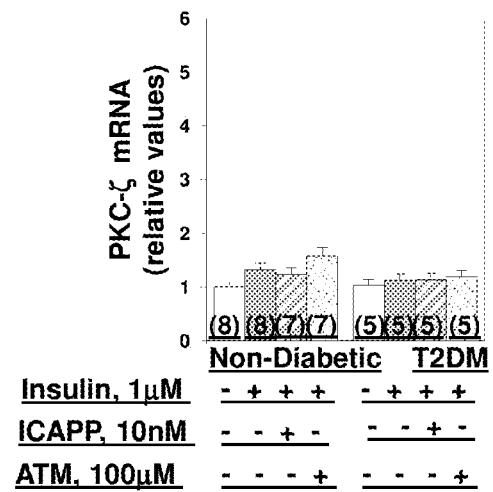
Figure 3E:
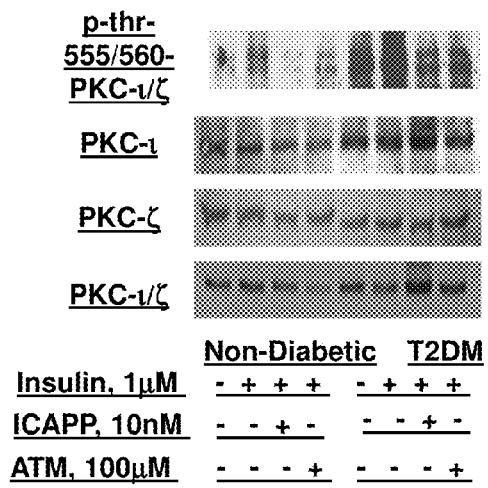
Figure 3F:
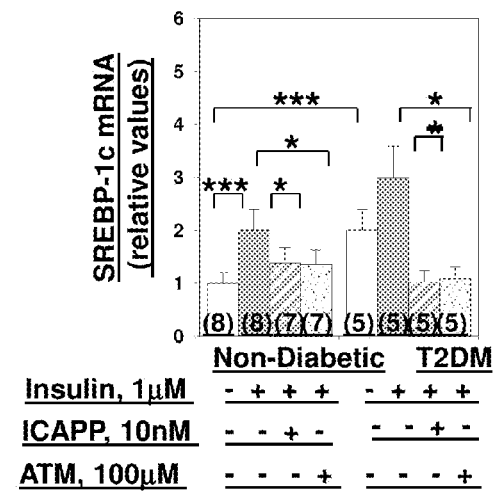
Figure 3G:
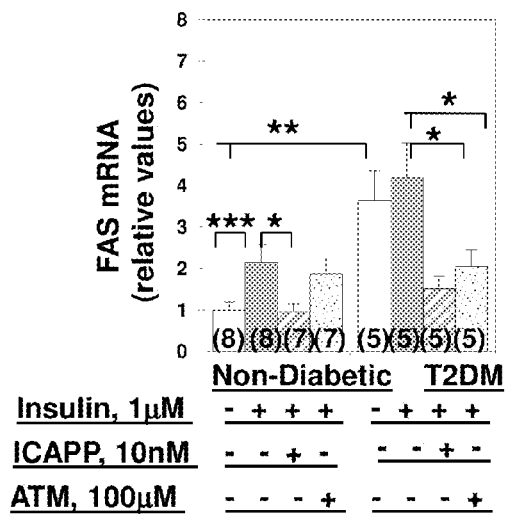
Figure 3H:
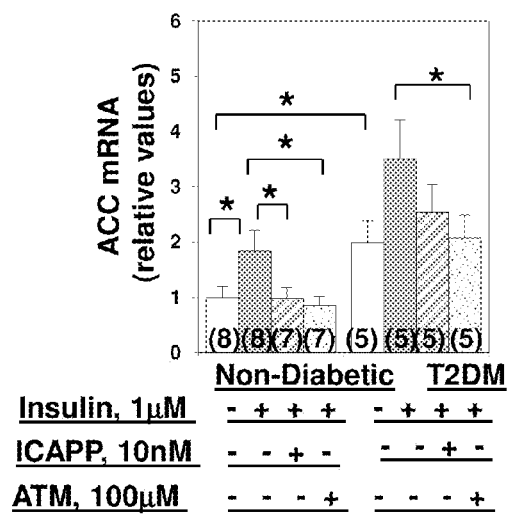

As with mRNA, hepatocyte $PKC_{-\iota}$ protein levels were increased 2-fold (1±0.04 (mean±SEM; n=4; non-diabetic subjects) versus 2.07±0.05 (mean±SEM; n=4 T2DM subjects) relative units) (immunoblots, FIGS. 2C and 3E). Unlike $PKC_{-\iota}$, expression and levels of PKC-ζ were not significantly altered by insulin, T2DM, and aPKC inhibitors (FIG. 3D). Also, total aPKC was increased less than $PKC_{-\iota}$ (FIGS. 2C and 3A), reflecting the presence of sizable amounts of PKC-ζ in human hepatocytes and Akt levels were not significantly altered in T2DM hepatocytes (FIG. 2C).

To summarize, these findings suggested that in human hepatocytes insulin stimulates a feed-forward/positive-feedback cycle in which $PKC_{-\iota}$ activation is required for self-expression.

Expression of $PKC_{-\iota}$ in Muscles of Non-Diabetic and T2DM Humans: In contrast to hepatocytes, but, in keeping with reports of diminished aPKC levels in human T2DM muscle (Beeson et al., *Diabetes* 52:1926-1934, 2003; Kim et al., *Diabetes* 52:1935-1942, 2003), muscle $PKC_{-\iota}$ mRNA was diminished by 57% (1±0.14 (mean±SEM; n=5 non-diabetic subjects) vs. 0.43±0.07 (mean±SEM; n=5 T2DM subjects) relative units (P<0.05; ANOVA)) and muscle $PKC_{-\iota}$ protein was diminished by 52% (1±0.12 (mean±SEM; N=12; non-diabetic) vs. 0.48±0.08 (N=12; T2DMs) relative units (P<0.001; ANOVA)). Although not shown, in humans: in muscle, $PKC_{-\iota}$ mRNA and protein levels are much higher than those of PKC-ζ, and $PKC_{-\iota}$ and PKC-ζ mRNA and protein levels in liver are much higher than those in muscle.

Levels of IRS-1 and IRS-2 in Hepatocytes of Non-Diabetic and T2DM Humans: IRS-1 levels were diminished in T2DM hepatocytes by 61% (1±0.01 (mean±SEM; n=5 non-diabetic subjects) vs. 0.39±0.10 (mean±SEM; n=5 T2DM subjects) relative units (P<0.001; ANOVA) in T2DM hepatocytes (FIG. 2C). In contrast, IRS-2 levels were not significantly altered (FIG. 2C).

Example 3

Effects of aPKC Inhibitors in Human Hepatocytes

This example describes the effect of aPKC inhibitors on aPKC activity and aPKC-dependent processes in human hepatocytes.

Effects of aPKC Inhibitors in Human Hepatocytes: To further define the role of hepatic aPKC in the development of abnormalities in O/MS/T2DM two relatively specific aPKC inhibitors recently developed by high throughput screening methods were utilized. The first inhibitor was 1H-imidazole-4-carboxamide, 5-amino-1-[2,3-dihydroxy-4-[(phosphonooxy)methyl]cyclopentyl-[1R-(1a,2b,3b,4a)] (ICAPP), which binds specifically to the substrate-binding the site of $PKC_{-\iota}$, but not PKC-ζ (Pillai et al., *Int. J. Biochem. Cell Biol.* available online at doi:10.1016/j.biocel.2011.02.002). The second inhibitor was aurothiomalate (ATM), which binds to cysteine-69 in $PKC_{-\iota}$ (cysteine-68 in PKC-ζ), thereby inhibiting PB1 domain-dependent binding to effectors such as Par6 and other factors that mediate effects on a variety of downstream processes (Stallings-Mann et al., *Cancer Res.* 66:1767-1774, 2006; Erdogan et al., *J. Biol. Chem.* 281: 28450-28459, 2006; Fields et al., *Biochem. Soc. Trans.* 23:1996-2000. 2007; Regala et al., *Cancer Res.* 68:5888-5895, 2008). ATM does not directly inhibit $PKC_{-\iota}$, but, as shown herein, does diminish induced increases in aPKC activity in intact tissues. The latter findings suggest that PB1 binds as-of-yet undefined factors that are needed for enzymatic activation of aPKC in intact cells. Without being bound by theory, inhibitory effects of ATM in intact cells may be mediated in two ways, via inhibition of PB1-dependent scaffolding and inhibition of aPKC enzyme activity.

Figure 4A:
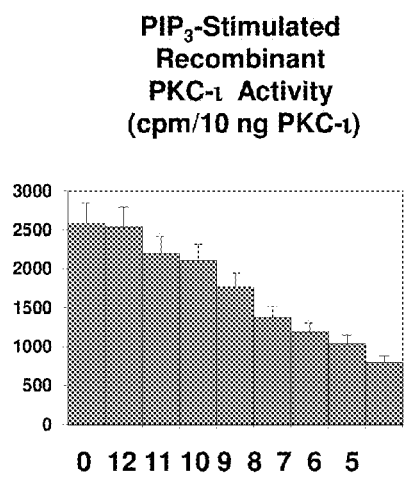
FIGS. 4A-K is a series of panels showing dose-related effects of the aPKC inhibitor ICAPP in hepatocytes of non-diabetic humans.
Figure 4B:
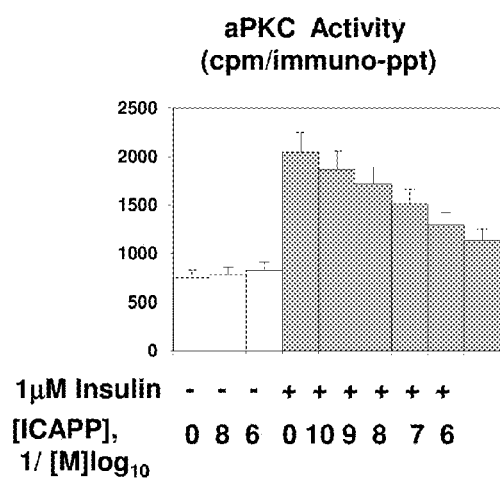
Figure 4C:
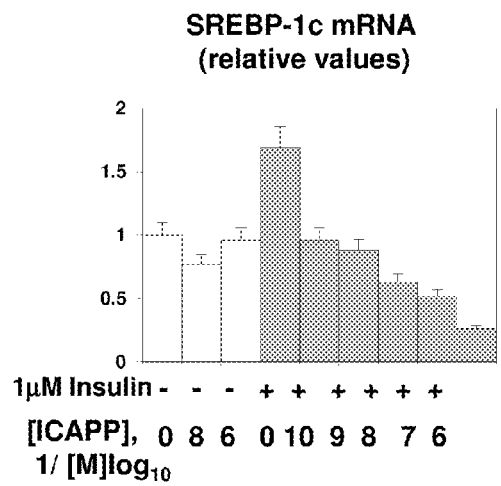
Figure 4D:
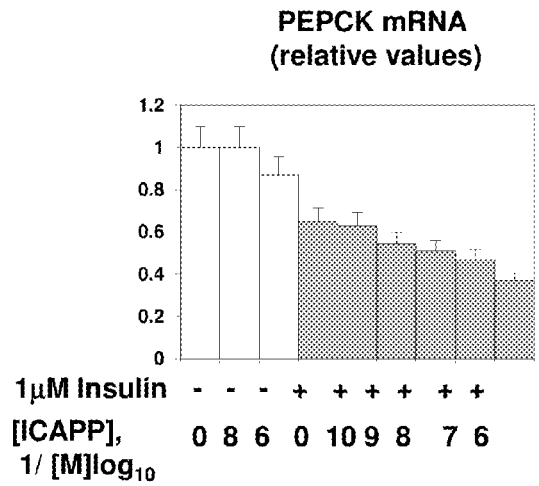

ICAPP potently inhibited ($IC_{50}$, approximately 10-100 nM) recombinant PKC-ι activated by phosphatidylinositol-3, 4,5-$(PO_4)_3$ ($PIP_S$) in vitro (FIG. 4A) and insulin-stimulated total (ι plus ζ) aPKC activity in intact human hepatocytes by approximately 50% (FIG. 4B). Residual aPKC activity probably reflects PKC-ζ, which is not inhibited by ICAPP; however, basal immunoprecipitable aPKC activity was resistant to ICAPP and probably reflects phosphorylation of the substrate used in the assay (a phosphorylatable analog of the PKC-ε pseudosubstrate peptide sequence) by a non-aPKC kinase.

Figure 5A:
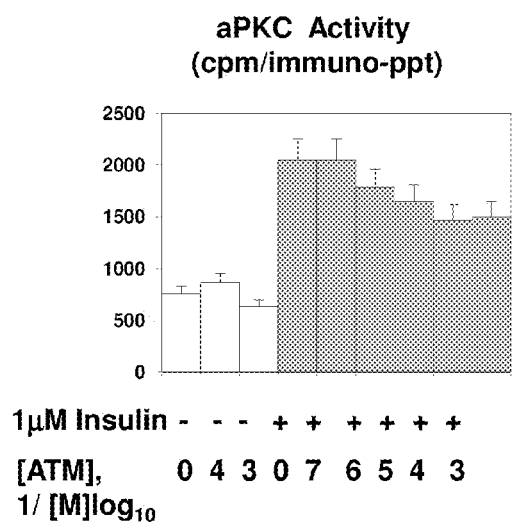
FIGS. 5A-I is a series of panels showing dose-related effects of the aPKC inhibitor ATM in hepatocytes of non-diabetic humans.
Figure 5B:
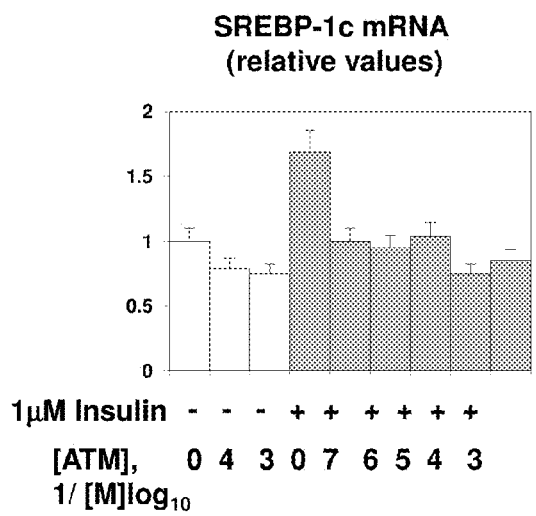
Figure 5C:
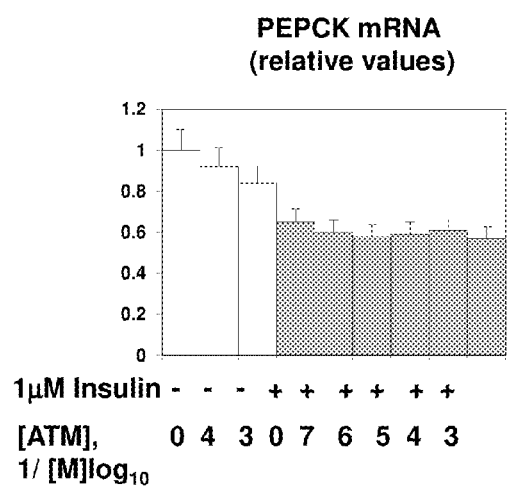

Like ICAPP, ATM diminished total aPKC activity in intact hepatocytes (FIG. 5A). Unlike ICAPP, ATM did not inhibit $PIP_3$-activated recombinant $PKC_{-\iota}$ or fully-activated aPKC immunoprecipitated from tissues previously stimulated by insulin. Thus, ATM inhibits the aPKC activation process in intact tissues, presumably by blocking PB1-dependent scaffolding to a required signaling complex, rather than by directly inhibiting the catalytic domain.

Figure 4E:
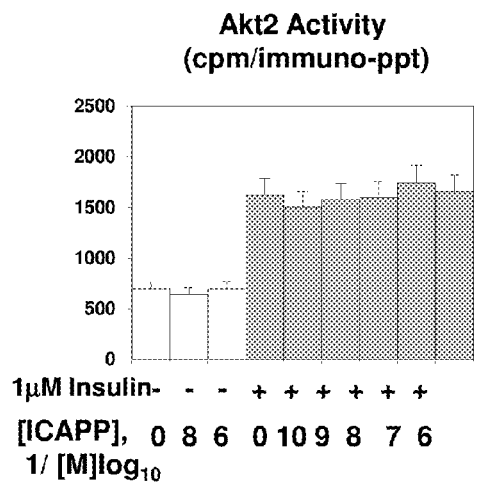
Figure 4F:
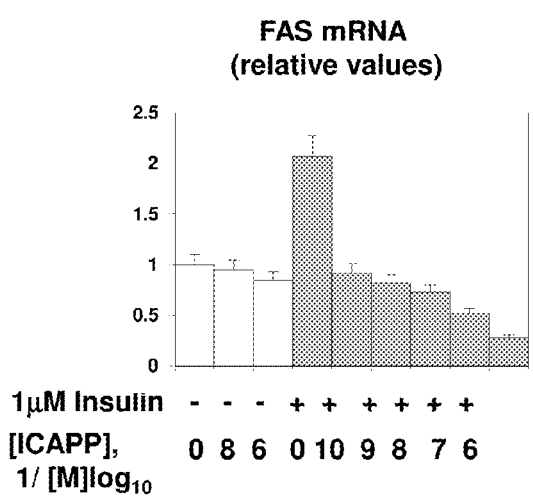
Figure 4G:
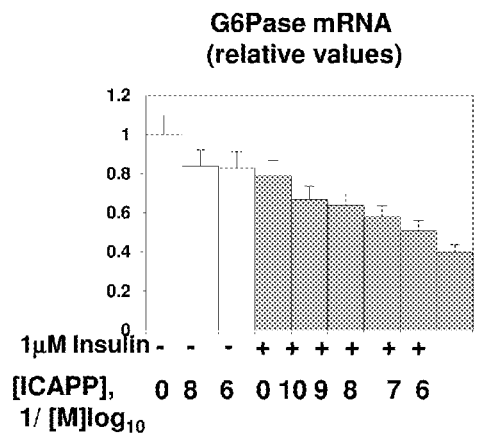
Figure 4H:
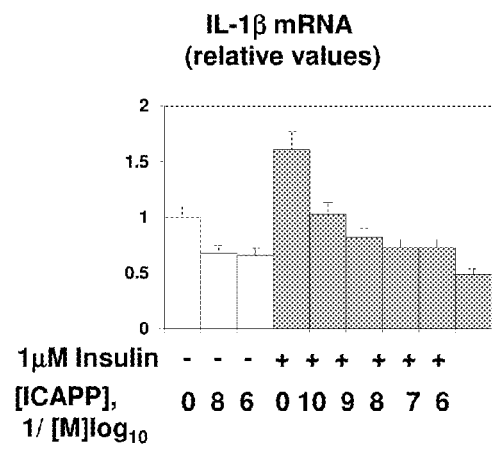
Figure 4I:
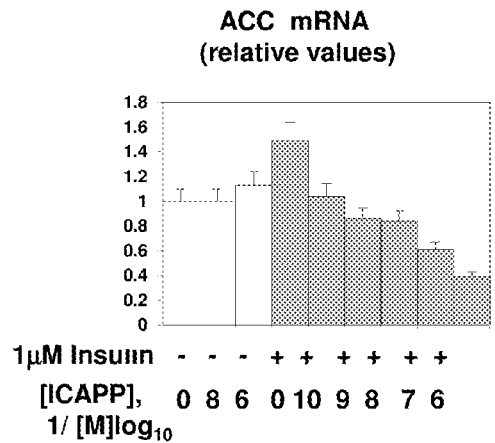
Figure 4J:
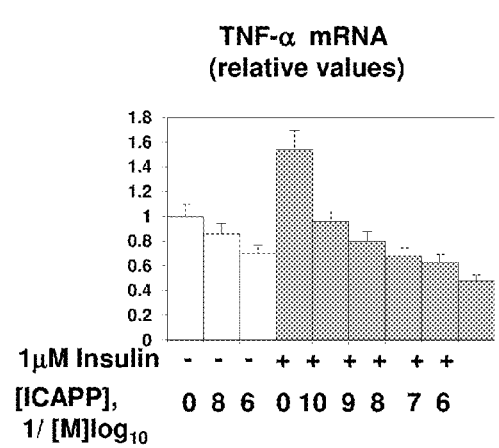
Figure 5D:
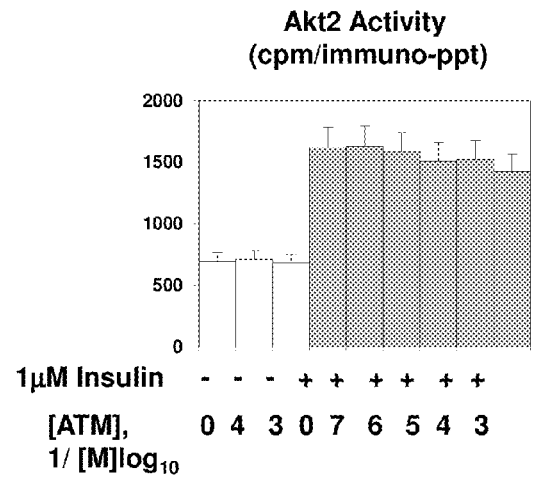
Figure 5E:
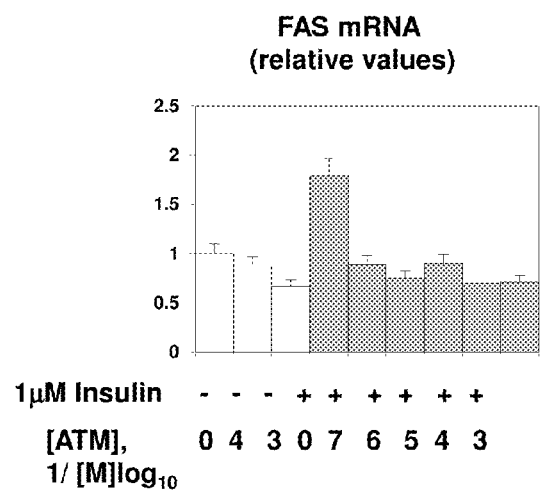
Figure 5F:
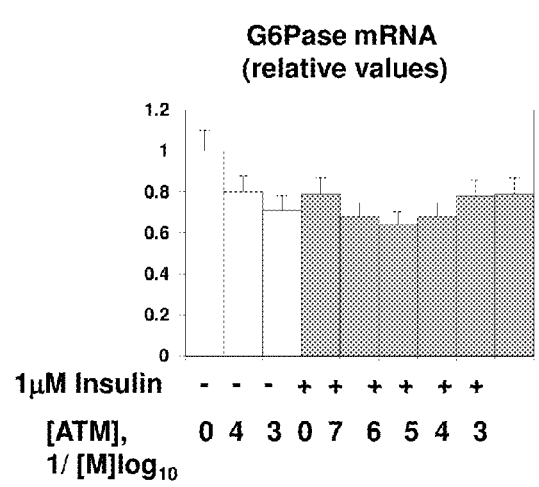
Figure 5G:
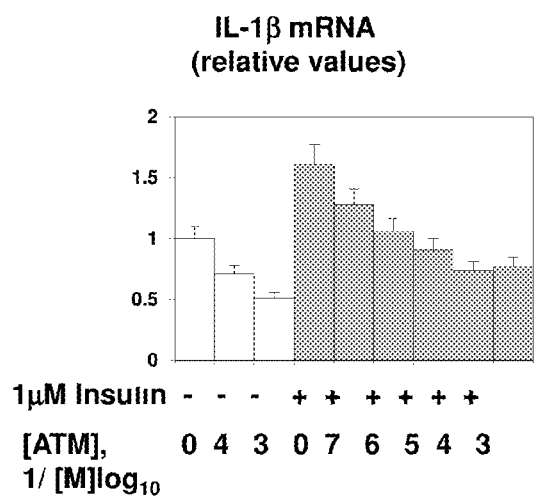
Figure 5H:
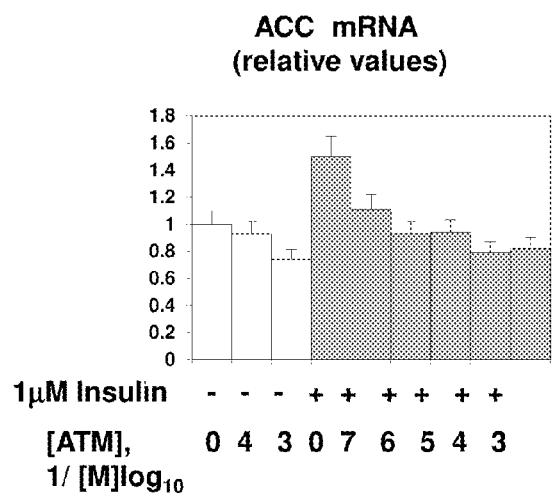
Figure 5I:
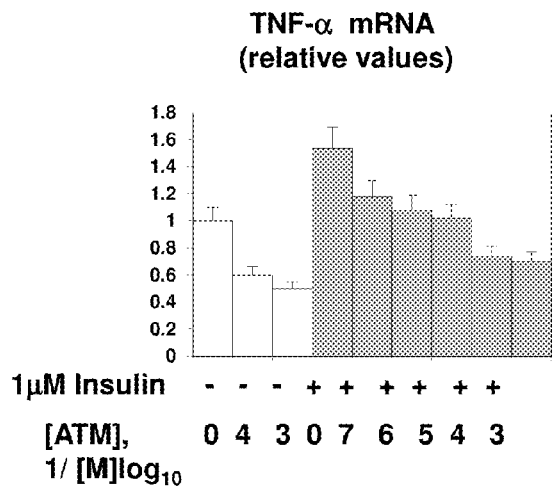

Also neither ICAPP nor ATM inhibited insulin-induced increases in Akt activity (FIGS. 4E and 5D). ICAPP did not inhibit increases in phosphoinositide-dependent kinase-1 (PDK1)-dependent phosphorylation of activation loop sites of $PKC_{-\iota}$/ζ (threonine-403/410). Both ICAPP and ATM diminished increases in phosphorylation of aPKC auto(trans) phosphorylation sites in intact hepatocytes (FIG. 3E). Finally, neither ICAPP nor ATM altered AMP-activated protein kinase activity.

Effects of aPKC Inhibitors on aPKC-Dependent Processes in Hepatocytes of Non-Diabetic and T2DM Humans: Accompanying increases in aPKC activity seen basally in T2DM hepatocytes, and in insulin-treated control and T2DM hepatocytes, expression of SREBP-1c and SREBP-1c-dependent enzymes, FAS and ACC, and NFκB-dependent cytokines, TNF-α and IL-1β, was increased (FIGS. 3F-H and 3K-L). Accompanying decreases in aPKC activity induced by ICAPP and ATM, expression of SREBP-1c, FAS, ACC, TNF-α, and IL-1β was diminished in hepatocytes of non-diabetic and/or T2DM humans (FIGS. 3F-H, 3K-L; 4C, 4F, 4H-J, 5B, 5E, and 5G-I). Unaltered expression of PKC-ζ served as a negative control for alterations in expression of other factors.

Figure 3I:
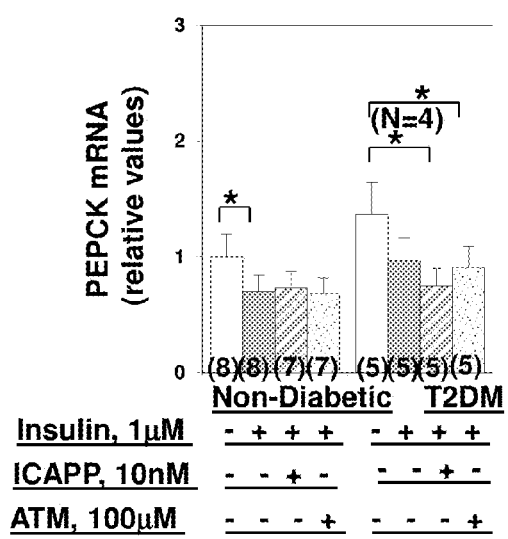
Figure 3J:
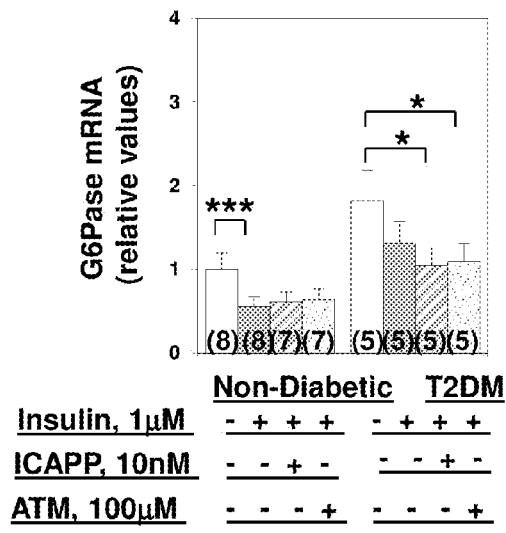
Figure 3K:
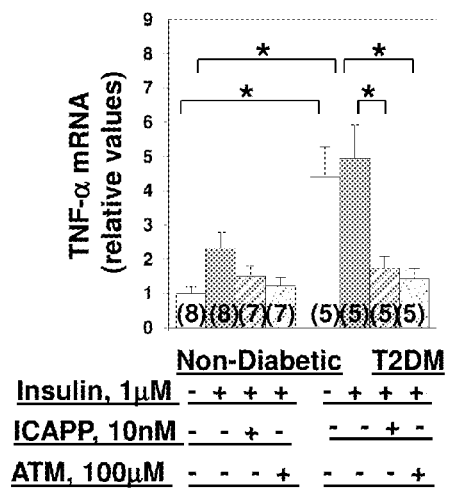
Figure 3L:
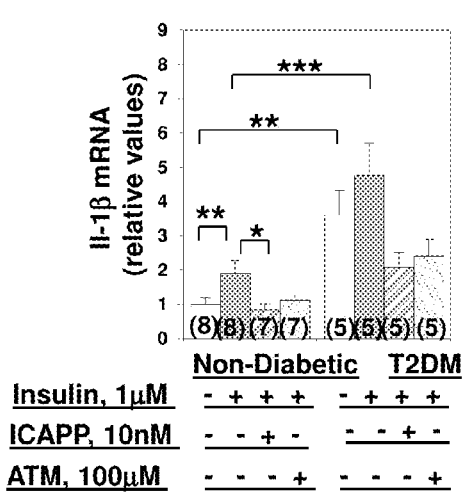
Figure 4K:
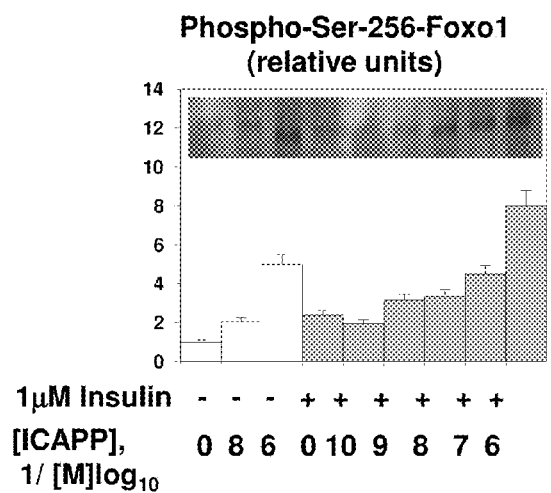

Insulin maintains blood glucose levels largely by decreasing expression of gluconeogenic enzymes, PEPCK and G6 Pase, thereby diminishing hepatic glucose output. Presumably, Akt mediates these inhibitory effects of insulin on expression of PEPCK and G6 Pase by phosphorylating ser-256 on FoxO1, thereby causing its nuclear exclusion and limiting its ability to promote expression of these gluconeogenic enzymes. It was therefore of interest to find that, in conjunction with decreased Akt activity, there were upward trends in basal expression and diminished effects of insulin on expression of PEPCK and G6 Pase in hepatocytes of T2DM humans (FIGS. 3I and 3J). Adenoviral-mediated inhibition of hepatic aPKC was previously found to provoke insulin-like decreases in fasting-dependent expression of PEPCK and G6 Pase in rodent liver (Sajan et al., *J. Lipid Res.* 50:1133-1145, 2009). Interestingly, ICAPP and ATM alone had insulin-like, or enhanced insulin, effects on FoxO1 phosphorylation (FIG. 4K) and expression of PEPCK and G6 Pase in hepatocytes of non-diabetic and T2DM humans (FIGS. 3I-J, 4D and 4G, and 5C and 5F).

In the dose-response studies shown in FIGS. 4 and 5, it should be noted that the presence of insulin in the medium during the initial 20-24 hours of culturing prior to the experimental period is likely to have raised the "basal" expression levels of SREBP-1c, FAS, ACC, TNF-α and IL-1β, and diminished the "basal" expression levels of PEPCK and G6 Pase. Also, ATM-induced inhibition of PB1-dependent scaffolding, as well as decreased aPKC enzyme activity, is likely to have contributed importantly to decreases in enzyme expression levels. Finally, "basal aPKC activity," as opposed to the increases seen with insulin treatment, was poorly or only partly responsive to aPKC inhibitors and probably contains some non-specific radioactivity or non-aPKC kinase activity. These factors, as well as the fact that the control of expression of these enzymes is multifactorial, may account for the lack of precise correlation between altered aPKC enzyme activity and enzyme expression. Nevertheless, ICAPP-induced decreases in aPKC activity correlated reasonably with decreases in enzyme expression Example 4

In vivo Effects of aPKC Inhibitors

This example describes the effect of aPKC inhibitors in a mouse model of obesity/metabolic syndrome/T2DM.

Both aPKC inhibitors were tested in a murine model of O/MS/T2DM, a heterozygous muscle-specific PKC-λ knockout (Het-MλKO) mice, wherein defective insulin-stimulated glucose transport in muscle leads to glucose intolerance, systemic insulin resistance, hyperinsulinemia, increased hepatic aPKC activity, activation of hepatic SREBP-1c and IKKβ/NFκB, and thus to increased expression of hepatic enzymes engaged in lipogenesis and cytokine production, and ultimately to hepatosteatosis, abdominal obesity, hypertriglyceridemia, fatty acidemia, hypercholesterolemia, hyperinsulinemia, glucose intolerance, fasting hyperglycemia, and diminished glucose-lowering effects of acutely administered insulin (Sajan et al., *J. Lipid Res.* 50:1133-1145, 2009; Farese et al., *J. Clin. Invest.* 117:2289-2301, 2007).

Figure 6A:
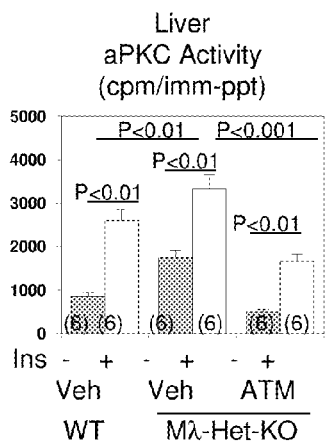
FIGS. 6A-R is a series of bar graphs showing effects of the aPKC inhibitor ATM in Het-MλKO mice.
Figure 6B:
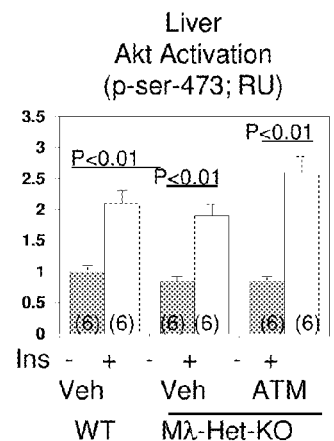
Figure 6C:
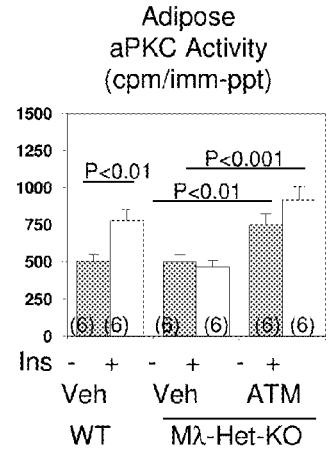
Figure 6D:
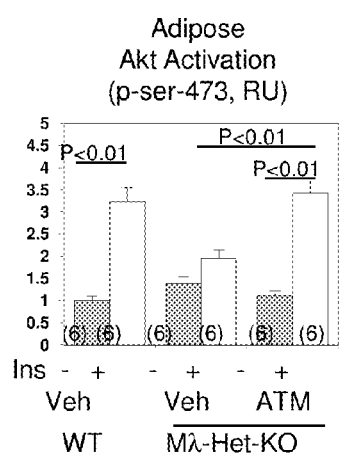
Figure 6E:
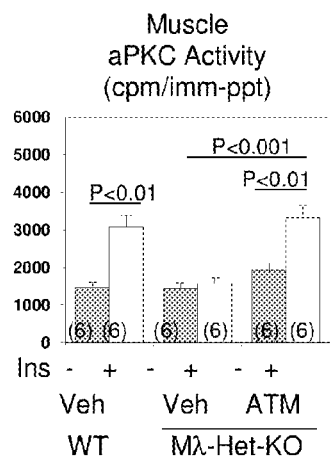
Figure 6F:
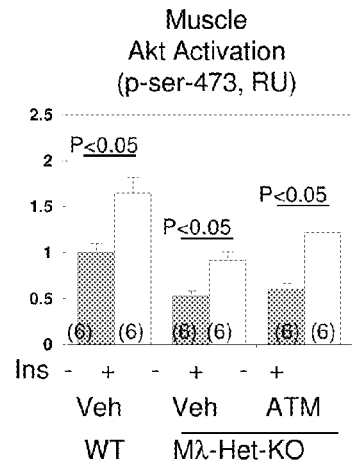

Effects of aPKC Inhibitor ATM in Het-MλKO Mice: Following 7-day treatment of Het-MλKO mice with ATM, "resting" (but elevated by hyperinsulinemia) and acute insulin-stimulated hepatic aPKC activities diminished by approximately 50% (FIG. 6A). In contrast, aPKC activation in muscle and adipose tissues increased significantly (FIGS. 6C and 6E), and hepatic Akt activation in liver, muscle and adipose tissues increased or trended upward (FIGS. 6B, 6D, and 6F). Note that in Het-MλKO mice, residual muscle aPKC is down-regulated but can be improved by hepatic aPKC inhibition (Sajan et al., *J. Lipid Res.* 50:1133-1145, 2009; Farese et al., *J. Clin. Invest.* 117:2289-2301, 2007).

Figure 6G:
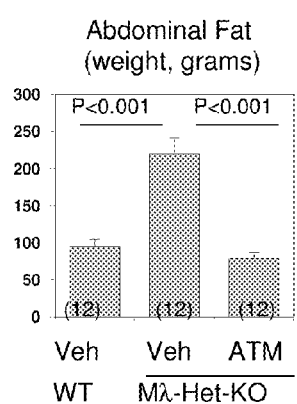
FIGS. 6G-L is a series of bar graphs showing clinical parameters (abdominal fat, serum cholesterol, serum and liver triglycerides, serum glucose, and serum insulin) in mice treated with ATM.
Figure 6H:
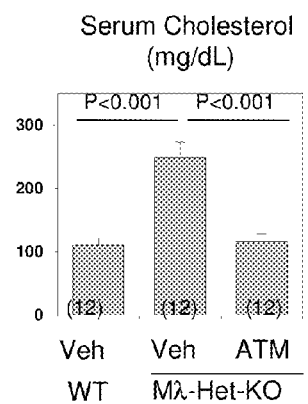
Figure 6I:
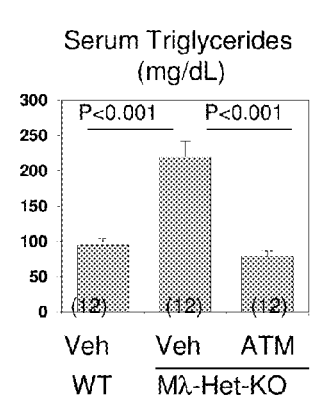
Figure 6J:
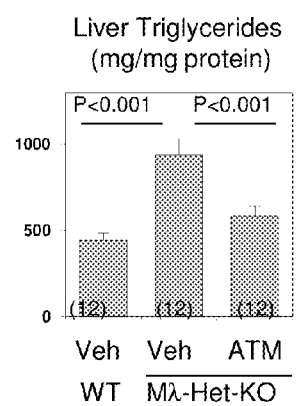
Figure 6K:
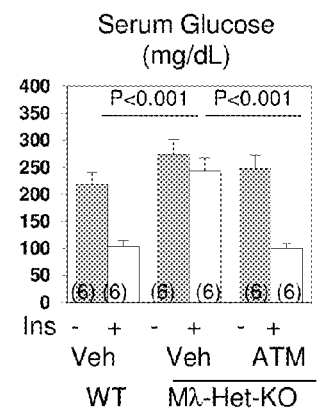
Figure 6L:
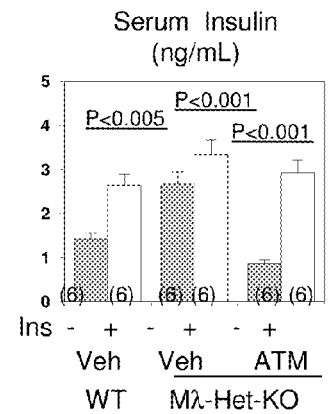
Figure 6M:
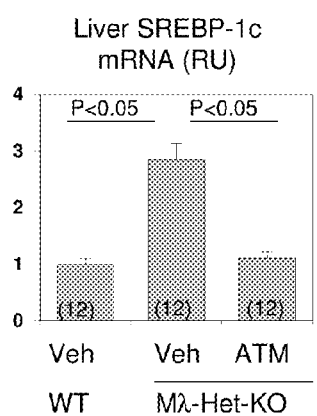
Figure 6N:
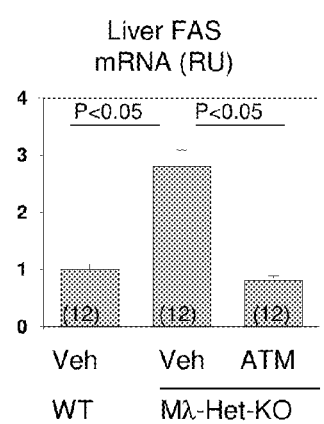
Figure 6O:
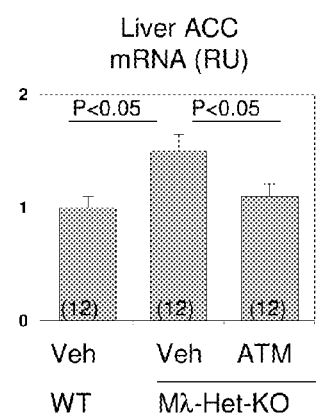
Figure 6P:
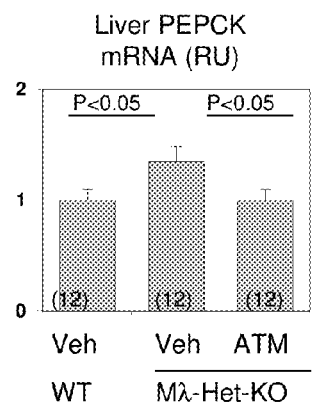
Figure 6Q:
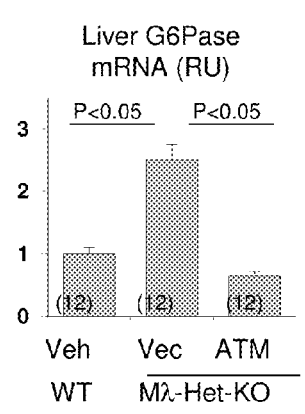
Figure 6R:
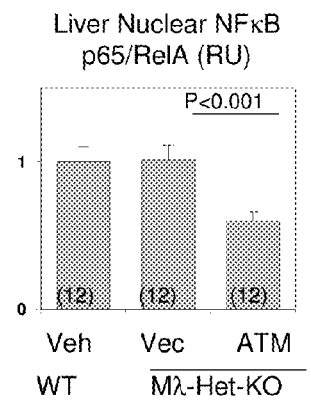

With decreases in hepatic aPKC activity, the following decreased, virtually to normal upon ATM treatment: (a) hepatic SREBP-1c, FAS, and ACC mRNAs (FIGS. 6M-O); (b) hepatic active nuclear NFκB/p65/RelA levels (FIG. 6R); (c) hepatic triglycerides (FIG. 6J); (d) abdominal fat content (FIG. 6G); (e) serum triglycerides and cholesterol (FIGS. 6H-I); (f) resting serum insulin levels (FIG. 6L); and (g) serum glucose levels following acute insulin treatment (FIG. 6K). Additionally, PEPCK and G6 Pase expression, which was increased in Het-MλKO liver, diminished with ATM treatment (FIGS. 6P-Q). Similarly, expression of TNF-α and IL-1β were increased 1.6-3 fold in Het-MλKO liver and normalized (P<0.05) after ATM treatment.

Germane to the ATM-induced improvement in abdominal obesity, 7-day food intake trended downward by 21% (0.61±0.06 (mean±SEM; N=12) in untreated vs. 0.48±0.03 (N=12) g food/g body-weight) in treated mice (P<0.07)). However, food intake is increased by 20% in untreated Het-MλKO mice (Farese et al., *J. Clin. Invest.* 117:2289-2301, 2007) and was not altered in wild type mice treated with ATM for 1-6 weeks. Also, glucose tolerance and insulin released during a 2-hour glucose tolerance test were not altered in wild type mice treated with ATM for 1-6 weeks, suggesting intactness of insulin secretion and glucose disposal.

Figure 7A:
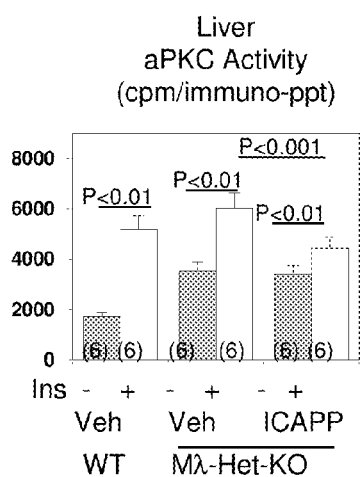
FIGS. 7A-R is a series of bar graphs showing effects of the aPKC inhibitor ICAPP in Het-MλKO mice.
Figure 7B:
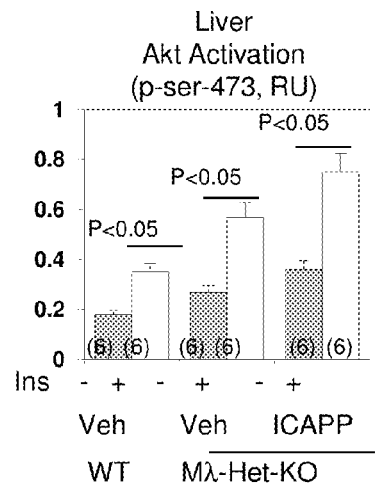
Figure 7C:
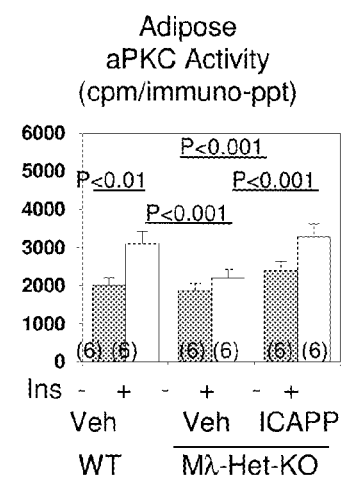
Figure 7D:
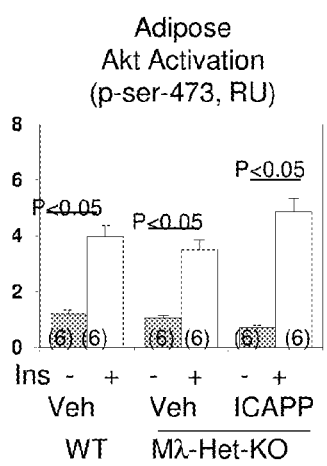
Figure 7E:
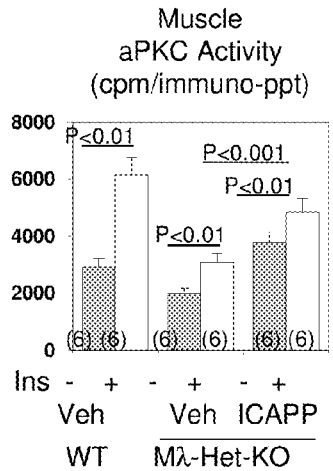
Figure 7F:
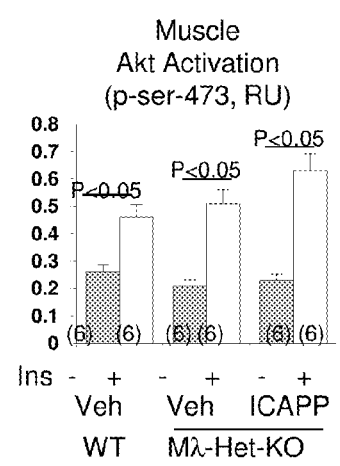
Figure 7G:
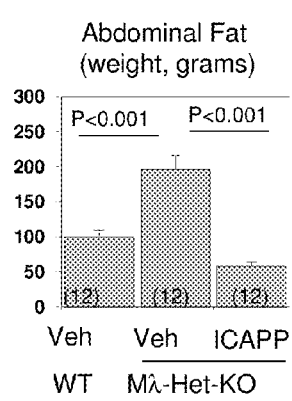
Figure 7H:
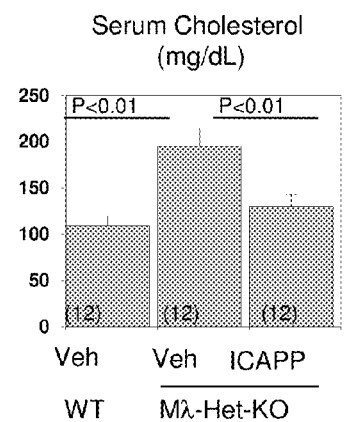
Figure 7I:
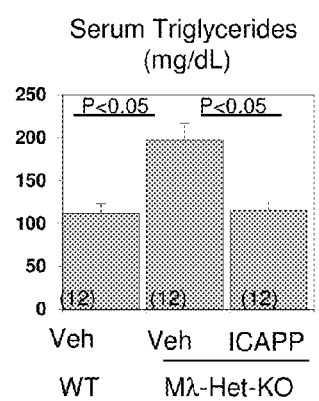
Figure 7J:
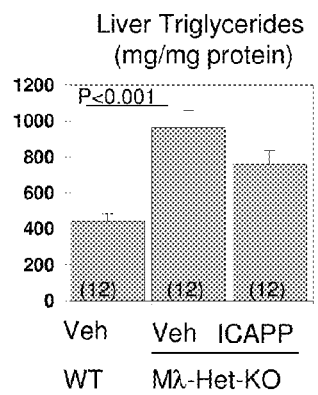
Figure 7K:
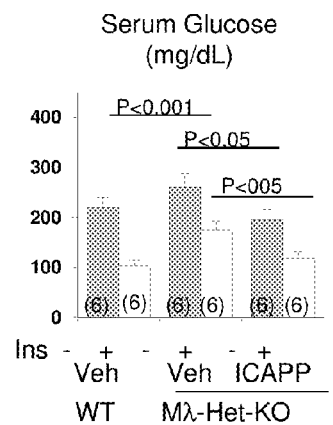
Figure 7L:
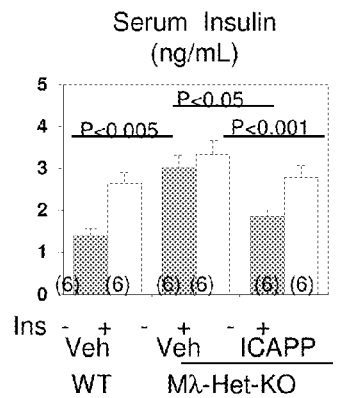
Figure 7M:
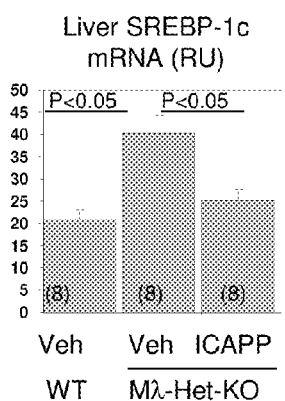
FIGS. 7M-Q is a series of bar graphs showing expression of lipogenic (SREBP-1c, FAS, and ACC) and glucogenic (PEPCK, G6 Pase) markers in liver. Het-MλKO mice were treated with vehicle (Veh) or ATM in vehicle (60 mg/kg body weight/day) for 7 days, and on the $8^{th}$ day the Het-MλKO mice, along with littermate wild type (WT) mice, were treated for 15 minutes by intraperitoneal injection with vehicle alone (−) or with vehicle containing insulin (1 U/kg body weight) (+). Values are mean±SEM of the number of mice shown in parentheses. RU=relative units. P values (ANOVA) reflect comparisons between indicated groups.
Figure 7N:
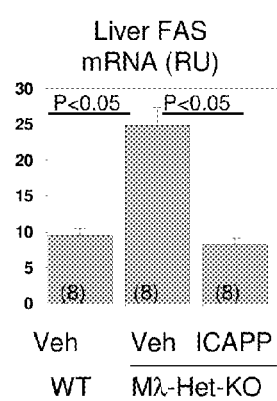
Figure 7O:
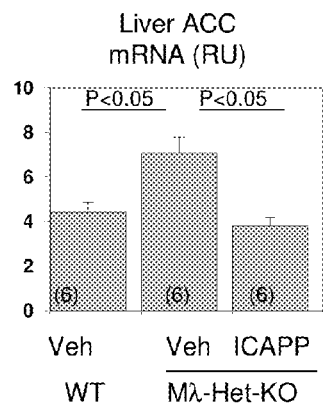
Figure 7P:
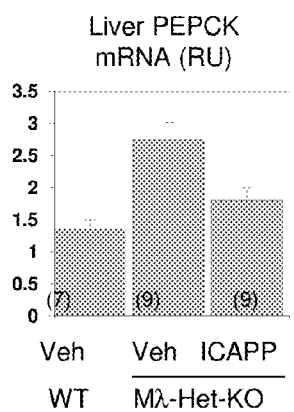
Figure 7Q:
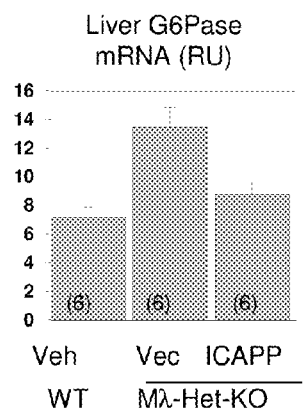
Figure 7R:
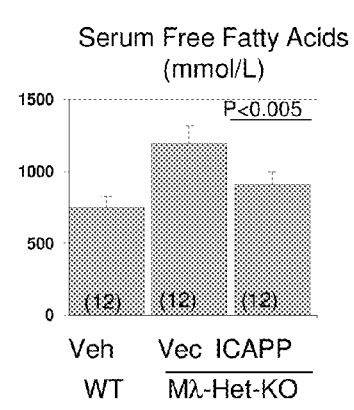

Effects of aPKC Inhibitor ICAPP in Het-MλKO Mice: As with ATM, 7-day treatment of Het-MλKO mice with ICAPP diminished insulin-stimulated hepatic aPKC, but not Akt, activity (FIGS. 7A and 7B). Furthermore, mRNA levels for hepatic SREBP-1c, FAS and ACC diminished to wild type levels after ICAPP treatment (FIGS. 7M-O), and this was accompanied by marked improvements in: abdominal fat content; hepatic triglyceride levels; serum levels of triglycerides, cholesterol and free fatty acids; basal serum insulin levels; and serum glucose levels, both before and following acute 15-min insulin treatment (FIGS. 7G-L and 7R). Also, acute (15-minute) aPKC and Akt activation by insulin increased significantly or trended upward in adipose and muscle tissues (FIGS. 7C-F), and expression of hepatic PEPCK and G6 Pase trended downward to or toward control levels after ICAPP treatment (FIGS. 7P-Q). Each of these alterations in muscle, adipose and liver tissues may have contributed to improvements in glucose homeostasis following ICAPP treatment. Unlike ATM, food intake was not altered in ICAPP-treated Het-MλKO mice.

Example 5

In vivo Effects of ICAPP on Insulin-Stimulated aPKC Activity

Wild type mice were treated with 1.5 mg/kg ICAPP subcutaneously and after 2-30 hours, the mice were treated with 1 U/kg insulin 15 minutes before euthanasia. aPKC activity was determined as described in Example 1.

ICAPP diminished insulin-stimulated aPKC activity in liver, but not in either muscle or adipose tissues of wild type mice (FIGS. 8A, B, and D). Also, ser-256 phosphorylation of hepatic FoxO1 was increased by ICAPP both basally and in response to insulin (FIG. 8C), reflecting intact or heightened hepatic Akt activation. The inhibition of hepatic aPKC and stimulatory effects on FoxO1 phosphorylation persisted unchanged for at least 30 hours after a single injection of ICAPP (FIGS. 8A-D).

Example 6

Figure 9A:
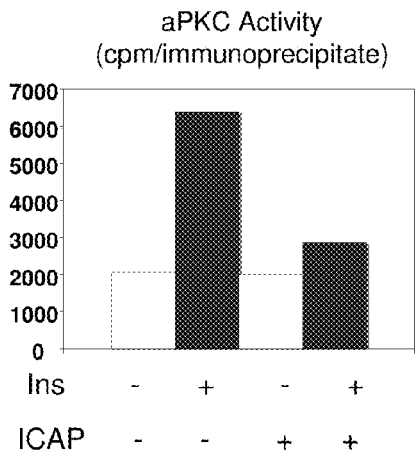
FIGS. 9A-F is a series of bar graphs showing aPKC activity (FIG. 9A) and expression of SREBP-1c, FAS, ACC, IL-1β, and TNF-α (FIGS. 9B-F, respectively) in non-diabetic human hepatocytes. Cells were treated with or without 100 nM insulin and 100 nM ICAP as indicated.
Figure 9B:
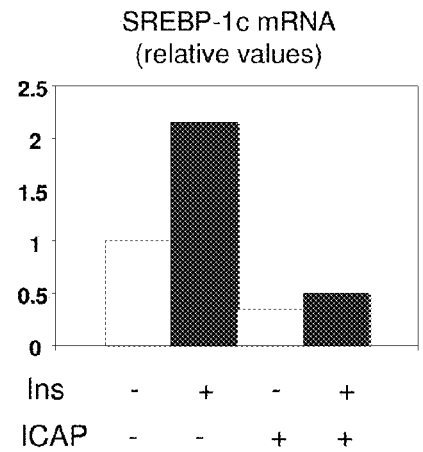
Figure 9C:
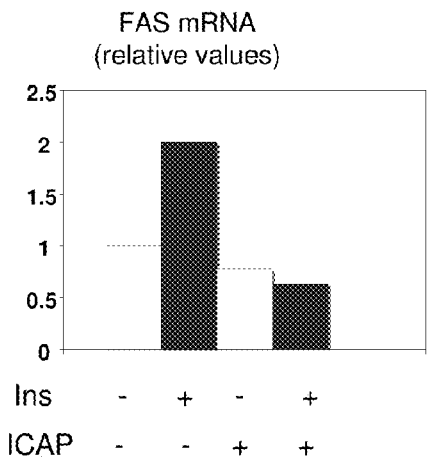
Figure 9D:
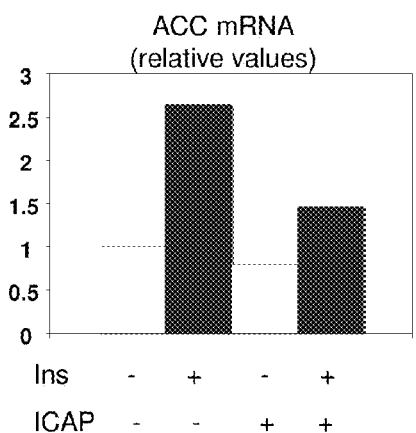
Figure 9E:
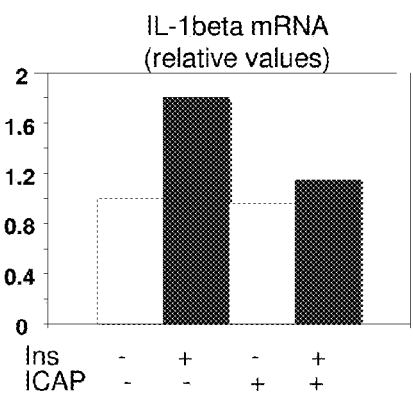
Figure 9F:
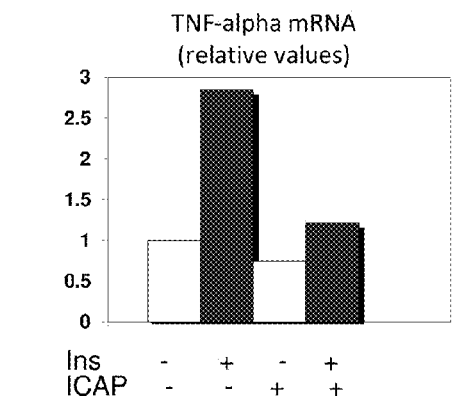

Effects of ICAP in Human Hepatocytes and a Mouse Model of Obesity/Metabolic Syndrome Hepatocytes of non-diabetic humans were incubated for 6 hours with or without 100 nM insulin and with or without 100 nM ICAP, after which aPKC activity and mRNA levels were measured. Insulin provoked increases in aPKC activity (FIG. 9A) and mRNA levels of lipogenic enzymes (SREBP-1c, FAS, and ACC; FIGS. 9B-D) and proinflammatory enzymes (IL-1β and TNF-α; FIGS. 9E and F). ICAP inhibited all of these insulin effects (FIGS. 9A-F), which are excessive in hyperinsulinemic states of obesity, metabolic syndrome and type 2 diabetes, and which contribute importantly in causing systemic insulin resistance, obesity, hepatosteatosis, hyperlipidemia, hypercholesterolemia, hyperglycemia and cardiovascular disease. Comparable results were obtained in hepatocytes of diabetic humans.

ICAP (0.5 mg/kg body weight/day×8 days) was administered s.c. to wild type mice and obese/diabetic Mk-Het KO mice. ICAP treatment inhibited hepatic aPKC (but not Akt) and diminished abdominal fat, basal and insulin-stimulated serum glucose levels, and serum levels of triglycerides and cholesterol in obese/type 2 diabetic heterozygous muscle-specific knockout mice (Table 2). Similar results were seen in repeat experiments.

TABLE 2

Effect of ICAP in wild type and obese/diabetic mice

| | Wild type (n = 8) | Untreated Mλ-Het KO (n = 12) | ICAP-treated Mλ-Het KO (n = 12) |
|---|---|---|---|
| Hepatic aPKC activity (cpm/immunoppt) | 1209 ± 235 | 1861 ± 250 | 1374 ± 128 |
| Hepatic Akt activity (cpm/immunoppt) | 532 ± 109 | 659 ± 83 | 1151 ± 226 |
| Abdominal fat (mg/g body weight) | 23.7 ± 2.3 | 38.9 ± 3.9 | 26 ± 3.2 |
| Ad lib-fed serum glucose (mg/dL) | 134 ± 3 | 171 ± 7 | 139 ± 20 |
| 10-min-post-insulin serum glucose (mg/dL) | 72 ± 9 | 136 ± 32 | 91 ± 8 |
| Serum triglycerides (mg/dL) | 111 ± 18 | 134 ± 12 | 104 ± 7 |
| Serum cholesterol (mg/dL) | 109 ± 7 | 130 ± 8 | 108 ± 10 |

Values are mean ± SEM.

Hepatic mRNA was isolated from ICAP-treated mice and expression of SREBP-1c, PEPCK, and G6 Pase were analyzed as described in Example 1. mRNA levels for hepatic SREBP-1c, PEPCK, and G6 Pase were decreased in ICAP-treated Mk-Het KO mice as compared to untreated Mk-Het KO mice (Table 3).

TABLE 3

Effect of ICAP on relative mRNA levels in obese/diabetic mice

| | Wild type | Untreated Mλ-Het KO | ICAP-treated Mλ-Het KO |
|---|---|---|---|
| SREBP-1c | 1 | 1.55 | 1.14 |
| PEPCK | 1 | 1.56 | 0.52 |
| G6Pase | 1 | 1.87 | 1.42 |

Example 7

Methods of Treating Metabolic Syndrome or Diabetes

This example describes methods that can be used to treat metabolic syndrome and/or diabetes in a subject. However, one skilled in the art will appreciate based on the teachings herein that methods that deviate from these specific methods can also be used to successfully treat metabolic syndrome or diabetes.

A subject who has been diagnosed with metabolic syndrome and/or diabetes is identified. Following subject selection, a therapeutically effective dose of a composition including a compound that specifically inhibits hepatic $PKC_\iota$ is administered to the subject. In an example, the composition includes ATM (such as sodium ATM or disodium ATM). In other examples, the composition includes ICAPP or a derivative thereof (such as the dephosphorylated form of ICAPP). The amount of the composition administered to prevent, reduce, inhibit, and/or treat metabolic syndrome and/or diabetes depends on the subject being treated, the severity of the disorder, and the manner of administration of the therapeutic composition. Ideally, a therapeutically effective amount of an agent is the amount sufficient to prevent, reduce, and/or inhibit, and/or treat the condition (e.g., metabolic syndrome and/or diabetes) in a subject without causing a substantial cytotoxic effect in the subject.

ATM is administered to a subject subcutaneously or intramuscularly. For example, ATM is administered at about 0.1-1 mg/kg daily, twice weekly, or weekly for at least 3 weeks. ICAPP or a derivative of ICAPP (such as ICAP) is administered to a subject subcutaneously or intramuscularly. For example, ICAPP or ICAP is administered at about 0.1-1 mg/kg daily, twice weekly, or weekly for at least 3 weeks.

A reduction in the clinical symptoms associated with metabolic syndrome, for example, decreased blood pressure, decreased triglycerides, increased HDL, or decreased insulin resistance (e.g., decreased fasting plasma glucose or decreased fasting plasma insulin or decreased QUICKI score) indicates the effectiveness of the treatment. A reduction in circulating endothelial adhesion markers and/or pro-inflammatory markers also indicates the effectiveness of the treatment. A reduction in one or more clinical symptoms associated with diabetes, for example, increased glucose tolerance, decreased insulin resistance (e.g., decreased fasting plasma glucose or decreased fasting plasma insulin or decreased QUICKI score), decreased triglycerides, decreased free fatty acids, decreased HbA1c, or a combination of two or more thereof, indicates the effectiveness of the treatment.

Example 8

Method for Treating Obesity

This example describes methods that can be used to treat obesity in a subject. However, one skilled in the art will appreciate based on the teachings herein that methods that deviate from these specific methods can also be used to successfully treat obesity.

In an example, a subject who is identified as obese (for example, an overweight or obese subject, such as a subject with a BMI of more than 25 kg/m$^2$) is selected. Following subject selection, a therapeutically effective dose of a compound that specifically inhibits hepatic $PKC_\iota$ is administered to the subject. In an example, the composition includes ATM (such as sodium ATM or disodium ATM). In other examples, the composition includes ICAPP or a derivative thereof (such as the dephosphorylated form of ICAPP). The amount of the composition administered to treat obesity depends on the subject being treated, the severity of the disorder, and the manner of administration of the therapeutic composition. Ideally, a therapeutically effective amount of an agent is the amount sufficient treat obesity in a subject without causing a substantial cytotoxic effect in the subject.

ATM is administered to a subject subcutaneously or intramuscularly. For example, ATM is administered at about 0.1-1 mg/kg daily, twice weekly, or weekly for at least 3 weeks. ICAPP (or a derivative thereof, such as ICAP) is administered subcutaneously or intramuscularly. For example, ICAPP or ICAP is administered at about 0.1-1 mg/kg daily, twice weekly, or weekly for at least 3 weeks.

A decrease in body weight, for example, decreased total body weight, decreased BMI, decreased waist circumference, decreased body fat, or a combination of two or more thereof, indicates the effectiveness of the treatment.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

I claim:

1. A method of treating obesity, metabolic syndrome, or diabetes in a subject, comprising:
   selecting a subject with obesity, metabolic syndrome, diabetes, or a combination of two or more thereof; and
   administering to the subject a therapeutically effective amount of a composition comprising a compound that specifically inhibits hepatic protein kinase C (PKC)-ι, thereby treating the obesity, metabolic syndrome or diabetes in the subject.

2. The method of claim 1, wherein the compound does not substantially inhibit PKC-ι in muscle or adipose tissue.

3. The method of claim 1, wherein the compound is not a protein or a nucleic acid.

4. The method of claim 1, wherein the compound comprises a thio-gold compound, 1H-imidazole-4-carboxamide, 5-amino-1-[2,3-dihydroxy-4-[(phosphonooxy)methyl]cyclopentyl]-[1R-(1α,2β,3β,4α)] (ICAPP), or 1H-imidazole-4-carboxamide 5-amino-1-[2,3-dihydroxy-4-[hydroxymethyl]cyclopentyl]-[1R-(1α,2β,3β,4α)](ICAP).

5. The method of claim 4, wherein the thio-gold compound comprises aurothiomalate, aurothioglucose, auranofin, or a combination of two or more thereof.

6. The method of claim 5, wherein the thio-gold compound comprises sodium aurothiomalate, disodium aurothiomalate, or a combination thereof.

7. The method of claim 5, wherein the aurothiomalate is administered at a dose of about 0.5-1 mg/kg.

8. The method of claim 1, wherein the compound comprises 1H-imidazole-4-carboxamide, 5-amino-1-[2,3-dihydroxy-4-[(phosphonooxy)methyl]cyclopentyl]-[1R-(1α,2β,3β,4α)] (ICAPP), or 1H-imidazole-4-carboxamide 5-amino-1-[2,3-dihydroxy-4-[hydroxymethyl]cyclopentyl]-[1R-(1α,2β,3β,4α)] (ICAP).

9. The method of claim 8, wherein the ICAPP or ICAP is administered at a dose of about 0.1-1 mg/kg.

10. The method of claim 1, wherein the composition is administered daily, once weekly, or twice weekly.

11. The method of claim 1, wherein treating obesity, metabolic syndrome or diabetes in the subject comprises increasing glucose tolerance, decreasing insulin resistance, decreasing serum triglycerides, decreasing serum free fatty acid levels, decreasing serum total cholesterol, decreasing serum low-density lipoprotein, increasing serum high-density lipoprotein, decreasing body weight, or a combination of two or more thereof in the subject as compared to a control.

12. The method of claim 11, wherein decreasing insulin resistance comprises decreasing plasma glucose levels, decreasing plasma insulin levels, or a combination thereof in the subject as compared to a control.

13. The method of claim 11, wherein increasing glucose tolerance comprises decreasing blood glucose levels in a glucose tolerance test in the subject as compared to a control.

14. The method of claim 1, wherein the subject is overweight or obese.

15. The method of claim 1, wherein the subject has type 2 diabetes.

16. The method of claim 1, wherein the composition further comprises a pharmaceutically acceptable carrier.

17. The method of claim 1, wherein the subject is a human.

18. The method of claim 1, further comprising providing to the subject a second therapy for treating obesity, metabolic syndrome, or diabetes, wherein the second therapy is selected from a lifestyle modification, an antihyperglycemic agent, insulin, glucagon-like peptide (GLP), a dipeptidyl peptidase-4 inhibitor, a thiazolidinedione, a lipid lowering compound, and a combination of two or more thereof.

19. The method of claim 18, wherein the second therapy comprises metformin.

20. A method of treating obesity, metabolic syndrome or diabetes in a subject, comprising:
   selecting a subject with obesity, metabolic syndrome, diabetes, or a combination of two or more thereof; and
   administering to the subject a therapeutically effective amount of 1H-imidazole-4-carboxamide, 5-amino-1-[2,3-dihydroxy-4-[(phosphonooxy)methyl]cyclopentyl]-[1R-( 1α,2β,3β,4α)](ICAPP) or 1H-imidazole-4-carboxamide 5-amino-1-[2,3-dihydroxy-4-[hydroxymethyl]cyclopentyl]-[1R-(1α,2β,3β,4α)] (ICAP), thereby treating obesity, metabolic syndrome or diabetes in the subject.

* * * * *

```
                          SEQUENCE LISTING

<160> NUMBER OF SEQ ID NOS: 40

<210> SEQ ID NO 1
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 1
atcggcgcgg aagctgtcgg ggtagcgtc                                       29

<210> SEQ ID NO 2
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 2
actgtcttgg ttgatgagct ggagcat                                         27

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 3
gaggacactc aagtggctga                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 4
gtgaggttgc tgtcgtctgt                                                 20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 5
gacttcatga atttgctgat                                                 20

<210> SEQ ID NO 6
<211> LENGTH: 20
<212> TYPE: DNA
<213> ORGANISM: Artificial Sequence
```

```
<220> FEATURE:
<223> OTHER INFORMATION: Synthetic oligonucleotide primer

<400> SEQUENCE: 6
aagctgaaag ctttctgtct                                              20

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 7
gacagcctgc cccaggcagt ga                                           22

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 8
ctggccacat ctcgagggtc ag                                           22

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 9
tgctgctcac tttccccacc ag                                           22

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 10
tctccaaagt ccacaggagg t                                            21

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 11
ttgacggacc ccaaaagatg                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 12
agaaggtgct catgtcctca                                              20
```

```
<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 13
acggcatgga tctcaaagac                                           20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 14
agatagcaaa tcggctgacg                                           20

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 15
catgcagagg cagagaaaac t                                         21

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 16
ttaggtcccg gtagatgatc c                                         21

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 17
tcactgacta cggcatgtgt aa                                        22

<210> SEQ ID NO 18
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 18
cgcagaaagt gctggttg                                             18

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide primer
```

```
<400> SEQUENCE: 19
tgaaagactt gctcgagatg t                                              21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 20
aaagaactta tagccccct t                                               21

<210> SEQ ID NO 21
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 21
cagccccact tcatcaagg                                                 19

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 22
actgttgcca agatggttcc g                                              21

<210> SEQ ID NO 23
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 23
tgtggacatg gtcacggac                                                 19

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 24
ggcatcaaac ctagacaggt c                                              21

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 25
tcgctttggg ggaaataaag tg                                             22
```

```
<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 26
accacctacg gatagaccgc                                            20

<210> SEQ ID NO 27
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 27
gctctgagga ggagaatgg                                             19

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 28
tgctcttggg tgacgataac                                            20

<210> SEQ ID NO 29
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 29
gctgaatgtc tgtctgtcac gaa                                        23

<210> SEQ ID NO 30
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 30
gcagaaggac aagacgtaga aga                                        23

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 31
caggccgcgt cagttgttgt                                            20

<210> SEQ ID NO 32
<211> LENGTH: 21
<212> TYPE: DNA
<213> ORGANISM: Artificial Sequence
<220> FEATURE:
<223> OTHER INFORMATION: Synthetic oligonucleotide primer
```

```
<400> SEQUENCE: 32
ccggagcgtt gcagttcagt g                                              21

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 33
cgccaccacg ctcttctg                                                  18

<210> SEQ ID NO 34
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 34
acggcgatgc ggctgatg                                                  18

<210> SEQ ID NO 35
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 35
cggaaccccg aattacatc                                                 19

<210> SEQ ID NO 36
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 36
accagtccac gctgaacc                                                  18

<210> SEQ ID NO 37
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 37
ggctgcattc ttgctttca                                                 19

<210> SEQ ID NO 38
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 38
tgtcgctgca tatgaaacat t                                              21
```

-continued

```
<210> SEQ ID NO 39
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 39
cgtgattagt gatgatgaac cag                                              23

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 40
cgagcaagac gttcagtcct                                                  20
```